(12) United States Patent
Suthers et al.

(10) Patent No.: US 6,852,517 B1
(45) Date of Patent: Feb. 8, 2005

(54) PRODUCTION OF 3-HYDROXYPROPIONIC ACID IN RECOMBINANT ORGANISMS

(75) Inventors: Patrick F. Suthers, Madison, WI (US); Douglas C. Cameron, N. Plymouth, MN (US)

(73) Assignee: Wisconsin Alumni Research Foundation, Madison, WI (US)

( * ) Notice: Subject to any disclaimer, the term of this patent is extended or adjusted under 35 U.S.C. 154(b) by 491 days.

(21) Appl. No.: 09/830,751

(22) PCT Filed: Aug. 30, 2000

(86) PCT No.: PCT/US00/23878

§ 371 (c)(1),
(2), (4) Date: Sep. 10, 2002

(87) PCT Pub. No.: WO01/16346

PCT Pub. Date: Mar. 8, 2001

Related U.S. Application Data

(60) Provisional application No. 60/151,440, filed on Aug. 30, 1999.

(51) Int. Cl.[7] .............................. C12P 7/62; C12N 9/00; C12N 1/20; C12N 15/00; C07H 21/04
(52) U.S. Cl. ....................... 435/135; 435/183; 435/190; 435/252.3; 435/320.1; 435/252.33; 536/23.2
(58) Field of Search .............................. 435/135, 252.3, 435/320.1, 183, 190, 252.33; 536/23.2

(56) References Cited

U.S. PATENT DOCUMENTS

| | | | |
|---|---|---|---|
| 4,962,027 A | 10/1990 | Slininger et al. | 435/147 |
| 5,164,309 A | 11/1992 | Gottschalk et al. | 435/158 |
| 5,254,467 A | 10/1993 | Kretschmann et al. | 435/158 |
| 5,413,960 A | 5/1995 | Dobrogosz et al. | 435/189 |
| 5,599,689 A | 2/1997 | Haynie et al. | 435/42 |
| 5,633,362 A | 5/1997 | Nagarajan et al. | 536/23.1 |
| 5,686,276 A | 11/1997 | Laffend et al. | 435/158 |
| 6,329,183 B1 * | 12/2001 | Skraly et al. | 435/135 |

FOREIGN PATENT DOCUMENTS

| | | |
|---|---|---|
| WO | WO 98/21340 | 5/1998 |
| WO | WO 99/28480 | 6/1999 |

OTHER PUBLICATIONS

Tang et al., *Immunochemical Properties of NAD[+]– Linked Glycerol Dehydrogenases from Escherichia coli and Klebsiella pneumoniae*, 152, No. 3, J. Bacteriol. 1169–1174 (1982).
Barbirate et al., *Anaerobic pathways of glycerol dissimilation by Enterobacter agglomerans CNCM 1210: limitations and regulations*, 143, Microbiology 2423–2432 (1997).
Cameron et al., *Metabolic Engineering of Propanediol Pathways*, 14 Biotechnol. Prog. 116–125 (1998).
Tong et al., *1,3–Propanediol Production by Escherichia coli Expressing Genase from the Klebsiella pnuemoniae dha Regulon*, 57, No. 12, Appl. Environ. Microbiol. 3541–3546 (1991).
Tong and Cameron, *Enhancement of 1,3–Propanediol Production by Cofermentation in Escherichia coli Expressing Klebsiella pneumoniae dha Regulon Genes*, 34/35 Appl. Biochem. Biotechnol. 149–159 (1992).
Cameron and Tong, *Cellular and Metabolic Engineering*, 38, Appl. Biochem. Biotechnol. 105–140 (1993).
Skraly et al. *Construction and Characterization of a 1,3–Propanediol Operon*, 64, No. 1, Appl. Environ. Microbiol. 98–105 (1998).
Skraly and Cameron, *Purification and Characterization of a Bacillus licheniformis Phosphatase Specific for D–α–Glycerophosphate*, 349, No. 1, Archives of Biochem. Biophys. 27–35 (1998).
Skraly, *Polyhydroxyalkannates Produced by Recombinant E. coli*, Poster at Enginnering Foundation Conference: Metabolic Engineering, entire document (1998).

* cited by examiner

*Primary Examiner*—Tekchand Saidha
(74) *Attorney, Agent, or Firm*—Quarles & Brady LLP

(57) ABSTRACT

The production of 3-hydroxypropionic acid (3-HP) from glycerol in a bacterial host is described. 3-HP is a useful feedstock for the production of polymeric materials. The genetic engineering of a bacterial host with two enzymes is sufficient to enable production of 3-HP. One enzyme is a glycerol dehydratase and the other is an aldehyde dehydrogenase.

8 Claims, No Drawings

PRODUCTION OF 3-HYDROXYPROPIONIC ACID IN RECOMBINANT ORGANISMS

CROSS-REFERENCE TO RELATED APPLICATIONS

This application claims priority from U.S. Provisional Patent Application Ser. No. 60/151,440 filed Aug. 30, 1999.

STATEMENT REGARDING FEDERALLY SPONSORED RESEARCH OR DEVELOPMENT

The research project which gave rise to the invention described in this patent application was supported by EPA grant R824726-01. The United States Government may have certain rights in this invention.

BACKGROUND OF THE INVENTION

The technology of genetic engineering allows the transfer of genetic traits between species and permits, in particular, the transfer of enzymes from one species to others. These techniques have first reached commercialization in connection with high-value added products such as pharmaceuticals. The techniques of genetic engineering are equally applicable and cost effective when applied to genes and enzymes which can be used to make basic chemical feedstocks.

A metabolic pathway of interest exists in the bacteria *Klebsiella pneumoniae*, which has the ability to biologically produce 3-hydroxypropionaldehyde from glycerol. Native microorganisms have the ability to produce 1,3-propanediol from glycerol as well. Commercial interests are exploring the production of 1,3-propanediol from glycerol or glucose, in recombinant organisms which have been engineered to express the enzymes necessary for 1,3-propanediol production from other organisms.

3-hydroxypropionic acid CAS registry Number [503-66-2] (abbreviated as 3-HP) is a three carbon non-chiral organic molecule. The IUPAC nomenclature name for this molecule is propionic acid 3-hydroxy. It is also known as 3-hydroxypropionate, β-hydroxpropionic acid, β-hydroxypropionate, 3-hydroxypropionic acid, 3-hydroxypropanoate, hydracrylic acid, ethylene lactic acid, β-lactic acid and 2-deoxyglceric acid. Applications of 3-HP include the manufacture of absorbable prosthetic devices and surgical sutures, incorporation into beta-lactams, production of acrylic acid, formation of trifluromethylated alcohols or diols, polyhydroxyalkonates, and co-polymers with lactic acid. 3-HP for commercial use is now commonly produced by organic chemical syntheses. The 3-HP produced and sold by these methods is relatively expensive, and it would be cost prohibitive to use it for the production of monomers for polymer production. As discussed below, some organisms are known to produce 3-HP. However, there is not yet available a catalog of genes from these organisms and thus the ability to synthesize 3-HP using the enzymes natively responsible for the synthesis of that molecule in the native hosts which produce it does not now exist.

In addition to its commercial utility, 3-HP it is found in a number of biological processes, notably including many naturally occurring bio-polymers. Poly(3-hydroxybutyrate) (PHB) is the most abundant member of the microbial polyesters which contain hydroxy monomers termed polyhydroxyalkonates (PHAs). PHB has utility as a biodegradable thermoplastic material and the material was first produced industrially in 1982.

The majority of published research on PHA's that contain 3-HP has concentrated on two bacterial sources: *Ralstonia eutropha* ("*Alcaligenes eutrophus*") and *Pseudomonas oleovorans*. Both *Ralstonia eutropha* and *Pseudomonas oleovorans* are able to grow on a nitrogen free media containing 3-hydroxy -propionic acid, 1,5-pentanediol or 1,7-heptanediol. When 3-HP is the major hydroxy-acid added to the growth media, poly(3-hydroxybutyrate-co-3-hydroxypropionic acid) is formed containing 7 mol % 3-hydroxypropionic acid. These cells also store 3 mol %, 3-hydroxypropionic acid poly(3-butyrate-co-3-hydroxypropionic acid).

Recombinant systems have been used to create PHAs. An *E. coil* strain engineered to express PHA synthase from either *Ralstonia eutropha* or *Zoolgoea ramigera* produced poly(3-hydroxypropionic acid) when feed 1,3-propanediol. Skraly, F. A. "Polyhydroxyalkonates Produced by Recombinant *E. coli.*" Poster at Engineering Foundation Conference: Metabolic Engineering II, 1998. An *E. coli* strain that expressed PHA synthase (MBX820), when provided with the genes encoding glycerol dehydratase and 1,3-propanediol dehydratase from *K. pneumonia,* and 4-hydroxybutyral-CoA transferase from *Clostridium kluyveri*, synthesized PHB from glucose.

Glycerol dehydratase, found in the bacterial pathway for the conversion of glycerol to 1,3-propanediol, catalyzes the conversion of glycerol to 3-hydroxypropionaldehyde and water. This enzyme has been found in a number of bacteria including strains of *Citrobacter, Klebsiella, Lactobacillus, Entrobacter* and *Clostridium*. In the 1,3-propanediol pathway a second enzyme 1,3-propanediol oxido-reductase (EC 1.1.202) reduces 3-hydroxypropanaldehyde to 1,3-propanediol in a NADH dependant reaction. The pathway for the conversion of glycerol to 1,3-propanediol has been expressed in *E. coli*. Tong et al., *Applied and Environmental Microbiology* 57 (12)3541–3546. The genes responsible for the production of 1,3-propanediol were cloned from the dha regulon of *Klebsiella pneumoniae*. Glycerol is transported into the cell by the glycerol facilitator, and then converted into 3-hydroxy-propionaldehyde by a coenzyme $B_{12}$-dependent dehydratase. *E. coli* lacks a native dha regulon, consequently *E. coli* cannot grow aerobically on glycerol without an exogenous electron acceptor such as nitrate or fumarate.

Aldehyde dehydrogenases are enzymes that catalyze the oxidation of aldehydes to carboxylic acids. The genes encoding non-specific aldehyde dehydrogenases have been identified in a wide variety of organisms e.g.; ALDH2 from *Homo sapiens*, ALD4 from *Saccharomyces cerevisiae*, and from *E. coli* both aldA and aldB, to name a few. These enzymes are classified by co-factor usage, most require either $AND^+$, or $NADP^+$ and some will use either co-factor. The genes singled out for mention here are able to act on a number of different aldehydes and it likely that they may be able to oxidize 3-hydroxy-propionaldehyde to 3-hydroxypropionic acid.

BRIEF SUMMARY OF THE INVENTION

The present invention is intended to permit the creation of a recombinant microbial host which is capable of synthesizing 3-HP from a starting material of glycerol or glucose. The glycerol or glucose is converted to 3-hydroxypropionicaldehyde (abbreviated as 3-HPA) which is then converted to 3-HP. This process requires the so-called dhaB gene from *Klebsiella pneumoniae* which encodes the enzyme glycerol dehydratase any one of four different aldehyde dehydrogenase genes to convert 3-HPA to 3-HP. The four aldehyde dehydrogenase genes used were aldA from the bacterium *E. coli*, ALDH2 from humans, ALD4 from the yeast *Saccharomyces cerevisiae*, and aldB from *E coli*. The yeast gene appeared to give the best results.

It is an object of the present invention to provide a genetic construct which encodes glycerol dehydratase and aldehyde dehydrogenase enzymes necessary for the production of 3-hydroxypropionic acid from glycerol.

It is also an object of the present invention to provide a method for the production of 3-hydroxypropionic acid from glycerol.

Other features and advantages of the invention will be apparent from the following description of the preferred embodiment thereof and from the claims.

BRIEF DESCRIPTION OF THE SEVERAL VIEWS OF THE DRAWINGS

Not applicable.

DETAILED DESCRIPTION OF THE INVENTION

It is disclosed here that it is possible to introduce into a bacterial host genes encoding two enzymes and thus confer upon that host the ability to produce 3-HP from glycerol. The two necessary enzymes are glycerol dehydratase and aldehyde dehydrogenase. It is here reported that the two enzymes are both necessary and sufficient to enable a strain of a suitable host, such as a competent *E. coli* strain, to make 3-HP from glycerol. An exemplary gene encoding a glycerol dehydratase is known, the dhaB gene from *Klebsiella pneumoniae*, sequenced and rendered convenient to use. Several exemplary aldehyde dehydrogenases are known, and their sequences are presented here. From this information, it becomes practical to confer upon a bacterial host the ability to convert glycerol into 3-HP in a commercially reasonable manner.

It was not apparent before the completion of the work described here that these two diverse enzymes could be produced in a common host to produce the ability to make 3-HP. There are many known aldehyde dehydrogenase enzymes and genes, and the enzymes are known to have varying substrate specificities and efficiencies. There was not evidence, prior to the work described here, that the aldehyde dehydrogenase enzyme would work on the 3-hydroxypropionicaldehyde (3-HPA) substrate to create 3-HP. Without that knowledge, there was no data from which to predict the effectiveness of the 3-HP production studies described below. An additional uncertainty arises from the fact that the intermediate aldehyde, 3-HPA, is toxic to many bacterial host and thus the survival of the host is dependent upon the relative rates of enzymatic production and conversion of the aldehyde intermediate to non-toxic 3-HP.

A difficulty in the realization of the production of 3-HP desired here is that ribosome binding sites from non-native hosts are often ineffectual and lead to poor protein production and that many non-native promoters are often poorly transcribed and a bar to high protein expression. However, the inventors also recognized that a non-native promoter that is known to be very active and is inducible by the addition of a small molecule unrelated to the pathway being expressed is often a very efficient way to express and regulate the levels of enzymes expressed in hosts such as *E. coli*. To achieve high levels of regulated gene expression plasmids were constructed which placed the expression of all exogenous genes necessary for the production of 3-hydroxypropionic acid from glycerol under the regulation of the trc promoter. The trc promoter, is efficient, not native to *E. coli*, and inducible by the addition of IPTG.

The present specification describes a genetic construct for use in the production of 3-hydroxypropionic acid from glycerol. The genetic construct includes exemplary DNA sequences coding for the expression of a glycerol dehydratase and a DNA sequence coding for aldehyde dehydrogenase. The set of exemplary sequences necessary for the expression of glycerol dehydratase is collectively referred to as "dhaB". The set of sequences necessary for the expression of aldehyde dehydrogenase includes any one of four different genes which proved efficacious. The individual aldehyde dehydrogenase sequences referred to individually as ALDH4, ALD2, aldA and aldB.

Producing 3-hydroxypropionic Acid in a Foreign Host

In the work described below, the enzymes necessary for the production of 3-hydroxypropionic acid from glycerol in *E. coli* were expressed under the regulation of the trc promoter, a non-native promoter inducible by the addition of IPTG. The glycerol dehydratase was encoded by the dhaB gene from *Klebsiella pneumoniae*, the aldehyde dehydrogenases used was any one of four different genes (ALDH2 from *Homo sapiens*, ALD4 from *S. cerevisiae*, aldB from *E. coli* or aldA from *E. coli*). Expression of these genes coding for glycerol dehydratase and any one of the genes encoding an aldehyde dehydrogenases was sufficient to enable the construct to produce 3-HP when the fermentation media was supplemented with glycerol. In all of these constructs, the dhaB gene was downstream from the gene encoding the aldehyde dehydrogenase used, and expression of both genes was regulated by the trc promoter. This order, however, is not required and the order of the gens on a construct and the use of multiple constructs is possible.

In a minimal genetic construct made based on the data presented here, the only genetic elements present that would be necessary are the structural genes dhaB and an aldehyde dehydrogenase gene encoding a protein that efficiently catalyzes the oxidation of 3-hydroxypropionaldehyde to 3-hydroxypropionic acid, and non-native promoter sequences specifically selected to give the type of inducible control most appropriate for the context of the process in which the construct is to be used. Extraneous pieces of DNA, whether retained in the construct or added from other DNA sequences, would not necessarily be detrimental to effective 3-HP synthesis by the host organism, but would not be needed. Each sequence to be translated would necessarily be preceded by a ribosome binding site, functional in the selected host so that the messenger RNA(s) coding for the proteins of interest could be translated by ribosomes. Terminator sequences immediately downstream of each translated unit would also be necessary in some organisms, particularly in eukaryotes. The construct could be part of an autonomously replicating sequence, such as a plasmid or phage vector, or could be integrated into the genome of the host.

The structural genes and appropriate promoter(s) could be isolated by the use of restriction enzymes, by the polymerase chain reaction (PCR), by chemical synthesis of the appropriate oligonucleotides, or by other methods apparent to those skilled in the art or molecular biology. The promoter(s) would be derived from genomic DNA of other organism or from artificial genetic constructs containing promoters. Appropriate promoter fragments would be ligated into the construct upstream of the structural genes in any one of several possible arrangements.

The aldehyde dehydrogenase expressed would have: high specific activity towards 3-hydroxypropionaldehyde; be very stable in the host it is expressed in; be readily over expressed in the selected host; not be inhibited by either the substrates necessary for the reaction or the products formed by the reaction; be fully active under the fermentation conditions most favorable for the production of 3-hydroxypropionic acid and be able to use either $NAD^+$ or $NADP^+$.

One possible arrangement is the true operon, where one promoter is used to direct transcription in one direction of all necessary Open Reading Frames (ORFs). The entire message is then contained in one messenger RNA. The advantages of the operon are that it is relatively easy to construct, since only one promoter is needed; that is it is relatively simple to replace the promoter with another promoter if that would be desirable later; and that it assures that the two genes are under the same regulation. The main disadvantage of the operon scheme is that the levels of the expression of the two genes cannot be varied independently. If it is found that the genes, for optimal 3-hydroxypropionic acid synthesis, should be expressed at different levels, the operon in most cases cannot be used to realize this.

Another possible arrangement is the multiple-promoter scheme. Two or more promoters, with the same or distinct regulatory behavior, could be used to direct transcription of the genes. For example, one promoter could be used to direct transcription of dhaB and one to direct transcription of the gene encoding the appropriate aldehyde dehydrogenases. Because the genes theoretically can be transcribed and translated separately, a great number of combinations of multiple promoters is possible. Additionally, it would be most desirable to prevent the promoters from interfering with one another. This could be achieved either by placing two promoters into the construct such that they direct transcription in opposite directions, or by inserting transcriptional terminator sequences downstream of each separately transcribed unit. The main advantage of the multiple-promoter construct is that it permits independent regulation of as many distinct units as desired, which could be important. The disadvantages are that it would be more difficult to construct; more difficult to amend later; and more difficult to effectively regulate, since multiple changes in fermentation conditions would need to be introduced and might render the performance of the fermentation somewhat less predicable.

In any construct, the promoter sequence(s) used should be functional in the selected host organism and preferably provide sufficient transcription of the genes comprising the glycerol to 3-hydroxypropionic acid pathway to enable the construct to be adequately active in that host. The promoter sequence(s) used would also effect regulation of transcription of the genes enabling the glycerol to 3-HP pathway to be adequately active under the fermentation conditions employed for 3-HP production, and preferably they would be inducible, such that expression of the genes could be modulated by the inclusion in, or exclusion from, the fermentation of a certain agents or conditions.

A plausible example of the use of such a construct follows: one promoter, which induced by the addition of an inexpensive chemical (the inducer) to the medium, could control transcription of both the dhaB gene and the gene encoding the appropriate aldehyde dehydrogenase. The cells would be permitted to grow in the absence of the inducer until they accumulated to a predetermined level. The inducer would then be added to the fermentation and nutritional changes commensurate with the altered metabolism would be made to the medium as well. The cells would then be permitted to utilize the substrate(s) provided for 3-HP production (and additional biomass production if desired). After the cells could no longer use substrate to produce 3-HP, the fermentation would be stopped and the 3-HP recovered.

Genetic Sequences

To express glycerol dehydratase and a suitable aldehyde dehydrogenase, the two enzymes necessary for the production of 3-hydroxypropionic acid from glycerol, it is required that the DNA sequences containing the glycerol dehydratase and aldehyde dehydrogenase coding sequences be combined with at least a promoter sequence (preferably a non-native promoter although some native promoter activity may be present). An exemplary method of construction is described in the example below. To ensure that the present specification is enabling, the full sequences of the coding regions of genes for these enzymes is presented here.

Sequences 1, 3, 5 and 7 present different native genomic sequences for genes encoding aldehyde dehydrogenases.

SEQ ID NO:1 contains the full native DNA sequence encoding the ALD4 enzyme from *Saccharomyces cerevisiae*. The amino acid sequence of the protein is presented as SEQ ID NO:2.

SEQ ID NO:3 includes the DNA sequence for the human ALDH2 gene, again including the full protein coding region. The amino acid sequence for this human alcohol dehydrogenase is presented in SEQ ID NO:4.

SEQ ID NO:5 and 7 respectively present the full coding sequences from the *E. coli* genes aldA and aldB, both of which encode alcohol dehydrogenases. The amino acid sequences for the proteins encoded by the genes are presented in SEQ ID NO:6 and 8 respectively.

SEQ ID NO:9 contains the native genomic DNA sequence for the dhaB gene from the dha regulon of *Klebisiella pneumoniae*. The coding sequences for this complex regulon produces five polypeptides, which are presented as SEQ ID NOS:10 through 13, which together provide the activity of the glycerol dehydratase enzyme.

Each of these coding sequences can be used to make genetic constructs for the expression of the appropriate enzymes in a heterologous hosts. In making genetic constructs for expression of the genes in such hosts, it is contemplated that heterologous promoters will be joined to the coding sequences for the enzymes, but all that it required is that the promoters be effective for the hosts in which the genes are to be expressed. It is also contemplated and envisioned that significant variations in DNA sequence are possible from the native DNA coding sequences presented here. As is well known in the art, due to the degeneracy of the genetic code, many different DNA sequences can encode the expression of the same protein. So, when this document uses language specifying a DNA sequence encoding a protein, it is intended to encompass any DNA sequence which can be used to express that protein even if different from the genomic sequences presented here. It is also contemplated that conservative changes in the amino acid sequences of the proteins specified here can be made without departing from the present invention. In particular, deletions, additions and substitutions of one or more amino acids in a protein sequence can almost always be made without changing protein functionality. When the name of a protein is sued here, it is intended to be equally applicable to both such minor changes in amino acid sequence and to allelic variations in native protein sequence as occurs within the species named as well as other closely related species.

It is possible that many of the above DNA sequences could be truncated and still express a protein that has the same enzymatic properties. One skilled in the art of molecular biology would appreciate that minor deletions, additions and mutations may not change the attributes of the designated base pair sequences; many of the nucleotide of the designated base pair sequences are probably not essential for their unique function. To determine whether or not an altered sequence or sequences has sufficient homology with the designated base pairs to function identically, one would simply create the candidate mutation, deletion or alteration and create a gene construct including the altered sequence together with promoter and termination sequences. This gene construct could be tested as, described below, for the production of 3-HP from glycerol.

Certain DNA primers were used to isolate or clone the genomic DNA sequences used in the experiments described below. While the sequence information presented here is sufficient to enable the construction of expression plasmids incorporating the genes identified here, in order to redundantly enable the use of these genes, primers which may be used to isolated the genes from their native hosts are described below.

The primers aldA_L (SEQ ID NO:14), and aldA_R (SEQ ID NO:15), were used to amplify the 1513 bp aldA fragment from genomic E. coli DNA (strain MG1655, a gift from the Genetic Stock Center, New Haven, Conn.). The gel purified PCR fragment containing a DNA sequence coding for the expression of aldehyde dehydrogenase was inserted into NcoI-XhoI site of pSE380 (Invitrogen, San Diego, Calif.) to give pPFS3. The resulting plasmid contained aldA under the control of the trc promoter. This construct allowed for high-level expression of the aldA gene from E. coli under regulation of the trc promoter. Unless indicated otherwise all molecular biology and plasmid constructions were done in E. coli AG1 (Stratagene, La Jolla, Calif.).

The primers aldB_L (SEQ ID NO:20) and aldB_R (SEQ ID NO:21), were used to amplify the 1574 bp aldB fragment from genomic E. coli DNA (strain MG1655). The resulting PCR converted the TGA stop codon into a TAA stop codon. The gel-purified PCR fragment containing the DNA sequence sufficiently coding for the expression of aldehyde dehydrogenase was inserted into the KpnI-SacI site of pSE380 to give pPFS12.

The primers ALD4_L (SEQ ID NO:16), and ALD4_R (SEQ ID NO:17), were used to amplify the 1595 bp ALD4 fragment from S. cerevisiae DNA (strain YPH500). The gel-purified fragment containing a DNA sequence coding for the expression of aldehyde dehydrogenase was inserted into the KpnI-SacI site of pPFS3 to give pPFS8. The resulting plasmid contained mature ALD4 under control of the trc promoter.

The primers ALDH2_L (SEQ ID NO:18), and ALDH2_R (SEQ ID NO:19), were used to amplify the 1541 bp ALDH2 fragment from pT7-7::ALDH2, a gift from H. Weiner (Purdue University, West Lafayette, Ind.). The gel purified PCR fragment containing a DNA sequence sufficiently homologous to base pairs 22 to 1524, inclusive of SEQ ID NO:3 so as to code for the expression of aldehyde dehydrogenase was inserted in to the KpnI-SacI site of pSE380 to give pPFS7. This sequence was moved from pPFS7 into the KpnI-SacI site of pPFS3 to give pPFS9. The resulting plasmid contained mature ALDH2 under the control of the trc promoter.

The primers pTRC_L (SEQ ID NO:22), and pTRC_R )SEQ ID NO:23), were used to amplify the 540 bp fragment from pSE380. The gel purified PCR fragment was inserted into the HpaI-KpnI site of pPFS3 to give pPFS13. The resulting plasmid deleted the "native" ribosome binding site of pSE380 and a NcoI site (which contained an extraneous ATG start codon upstream of the cloned genes). The KpnI-SacI fragments of pPFS8, pPFS9, and pPSF12 were inserted into the KpnI-SacI site of pPFS13 to give pPFS14, pPFS15, and pPFS16, respectively.

Assay for Production of 3-HP

The efficacy of changes made as contemplated herein can be checked by the following tests. To test for the production of 3-HP, fermentation products can be quantified with a Waters Alliance Integrity HPLC system (Milford, Mass.) equipped with a refractive index detector, a photodiode array detector, and an Aminex HPX-87H (Bio-Rad, Hercules, Calif.) organic acids column. The mobile phase should be 0.01 N sulfuric acid solution (pH 2.0) at a flow rate of 0.5 mL/min. The column temperature should be set to 40° C. Compounds can be identified by determining if they co-elute with authentic standards. Prior to analysis, all samples should be filtered through 0.45 $\mu$M pore size membrane. (Gelman Sciences, Ann Arbor, Mich.). The fractions of the fermentation products collected using HPLC should be analyzed on a Varian Star 3400 CX, gas-chromatograph coupled to a Varian Saturn 3 mass spectrometer (GC-MS) (Walnut Creek, Calif.).

Assay for Enzyme Activity

Aldehyde dehydrogenase activity can be determined by measuring the reduction of $\beta$-NAD$^+$ at 25° C. with 3-hydroxypropionaldehyde as a substrate. All buffers should contain 1 mM ethylenediaminetetraacetic acid (EDTA), 0.1 mM Pefabloc SC (Boehringer Mannheim, Indianapolis, Ind.) and 1 mM Tris (carboxyethyl) phosphine hydrochloride (TCEP-HCL). For ALD4, the solution should contain 100 mM Tris HCL Buffer (pH 8.0), 100 mM KCl. For ALDH2 the solution should contained 100 mM sodium pyrophosphate (pH 9.0). For AldA and AldB, the solution should contain 20 mM sodium glycine (pH 9.5). A total of 3.0 mL of buffer should be added to quartz cuvettes and allowed to equilibrate to assay temperature. From 5 to 20 $\mu$L of cell extract should be added and background activity recorded after the addition of $\beta$-NAD$^+$ to a final concentration of 0.67 mM. The reaction should be started by the addition of substrate (either acetaldehyde, propionaldehyde, or 3-hydroxypropionaldehyde) to a final concentration of 2 mM. Assay mixtures should be stirred with micro-stirrers during the assays.

For aldehyde dehydrogenase activity assays, one unit is defined as the reduction of 1.0 $\mu$M of $\beta$-AND$^+$ per minute at 25° C. These reactions can be monitored by following the change in absorbence at 340 nm ($A_{340}$) at 25° C. on a Varain Carry-1 Bio spectrophotometer (Sugar Land, Tex.). Total protein concentrations in the cell extracts can be determined using the Bradford assay method (Bio-Rad, Hercules, Calif.) with bovine serum albumin as the standard.

EXAMPLES ps Plasmid Constructions

Klebsiella pneumoniae expresses glycerol dehydratase, an enzyme that catalyzes the conversion of glycerol to 3-hydroxypropionaldehyde, (dhaB) and 1,3-propanediol oxidoreductase an enzyme that catalyzes the conversion of 3-hydroxypropionaldehyde to 1,3-propanediol respectively (the gene product from dhaT). A plasmid encoding these two genes was created and expressed in E. coli (plasmid pTC53). The dhaT gene was deleted from pTC53 to create pMH34. The resulting plasmid still contained the DNA sequence complementary to base pairs 330 to 2153 inclusion of SEQ ID NO:9, the complement of base pairs 2166 to 2591, inclusive, of SEQ ID NO:9, and the complement of base pairs 3191 to 4858, inclusive, of SEQ ID NO:9, so as to code for the expression of glycerol dehydratase. The fragment of DNA encoding these sequences was excised from pMH34 by cutting it with SalI-XbaI, and the resulting fragment was gel purified (the purified fragment was gift from M. Hoffman of the University of Wisconsin—Madison). This DNA fragment was inserted into the SalI-XbaI site of pPFS13 to give pPFS17.

The resulting plasmid contained both the aldA and dhaB genes under the control of the trc promoter. Similarity, the gel-purified SalI-XbaI fragment from pMH34 was inserted into the SalI-XbaI sites of pPFS14, pPFS15, and pPFS16 to give pPFS18, pPFS19, and pPFS20, respectively. These plasmids contained ALD4, ALDH2, and aldB, respectively, as well as dhaB under the control of the trc promoter; in all of the constructs the dhaB gene were downstream of the gene encoding the aldehyde dehydrogenase.

Expression in E. coli

The efficacy of E. coli as a platform for the production of 3-HP from growth on glucose has been examined using a mathematical model developed for this purpose. The model was executed in two different ways assuming the conversion of one mole of glucose under either anaerobic or aerobic conditions either directly to 3-HP or to the production of 3-HP and ATP. The optimum yield under anaerobic conditions is 1 mole of 3-HP and 1 mole of lactate. The more realistic yield under anaerobic conditions is 0.5 moles of 3-HP, 1.5 moles of lactate and 1 mole of ATP. The optimum yield under aerobic conditions is 1.9 moles of 3-HP and 0.3 moles of $CO_2$. The realistic yield under aerobic conditions is 1.85 moles of 3-HP, 0.35 moles of $CO_2$ and 1 mole of ATP.

The effect of 3-HP concentration on E. coli strain MG1655 growth was measured. Cells were grown on standard media with and without the addition of up to 80 g/L of 3-HP. The best fit of these data demonstrated that 3-HP was only 1.4 times as inhibitory as lactic acid on the growth of E. coli. It is possible to economically produce lactic acid using E. coli, since 3-HP is only 1.4 times more inhibitory than lactic acid, it should be possible to use E. coli as a host for the commercial production of 3-HP.

Media and Growth Conditions

The standard media contained the following per liter: 6 g $Na_2HPO_4$, 3 g $KH_2PO_4$, 1 g $NH_4Cl$, 0.5 g NaCl, 3 mg $CaCl_2$, 5 g yeast extract (Difco Laboratories, Detroit, Mich.) and 2 mM $MgSO_4$. When necessary to retain plasmids ampicillin (100 mg/mL) was added to the media. Isopropyl-β-thiogalactopyranoside (IPTG) was added in varying amounts to induce gene expression. All fermentations were carried out in an incubator-shaker at 37 C and 200 rpm. Anaerobic fermentations were carried out in 500-mL anaerobic flasks with 300 mL of working volume. Inocula for fermentations were grown overnight in Luria-Bertani medium supplemented with ampicillin is necessary. The 300-mL fermentations were inoculated with 1.5 mL of the overnight culture. For enzyme assays, fermentations were incubated for 24 hours.

Over Expression of Aldehyde Dehydrogenase in E. coli.

Cells were harvested by centrifugation at 3000×g for 10 minutes at 4° C. with a Beckman (Fullerton, Calif.) model J2-21 centrifuge. Cell pellets were washed twice in 100 mM potassium phosphate buffer at pH 7.2 and re-suspended in appropriate assay resuspension buffer equal to 5× of the volume of the wet cell mass. The cells were homogenized using a French pressure cell. The homogenate was centrifuged at 40000×g for 30 minutes. The supernatant was dialyzed against the appropriate resuspension buffer using 10000 molecular weight cut-off pleated dialysis tubing (Pierce, Rockford, Ill.) at 4° C. Dialysis buffer was changed after 2 hours, and 4 hours, and dialysis was stopped after being allowed to proceed overnight.

E. coli AG1 cells transfected with the plasmids constructed to express the aldA, ALD4, ALDH2, or aldB genes were grown in 500-mL anaerobic flasks. Twelve hours after the fermentations were inoculated IPTG was added to induce enzyme expression. The cells were allowed to grow for an additional 12 hours then harvested and lysed as discussed above. The soluble fraction of the lysate was assayed for aldehyde dehydrogenase activity using the substrate 3-hydroxypropionicaldehyde in the buffer appropriate for the particular enzyme expressed The plasmid, aldehyde dehydrogenase expressed and specific activity measured (U/mg of protein) were as follows: pPFS13, aldA, 0.2; pPFS14, ALD4, 0.5, pPFS15, ALDH2, 0.3; and pPFS16, aldB.0.1. The control, E. coli strain AG1 harboring plasmid pSE380, encoded no exogenous aldehyde dehydrogenase activity and it had no detectable activity with 3-HP as substrate. It is clear from the activity assays that all four aldehyde dehydrogenases were expressed in E. coli. The aldehyde dehydrogenase cloned from Saccharomyces cerevisiae (ADH4) had the highest activity when 3-hydroxypropionaldehyde was used as the substrate (0.5 units/mg of protein).

E. coli cells transformed with plasmids expressing: aldehyde dehydrogenase; both aldehyde dehydrogenase and glycerol dehydratase, or neither gene; were grown and assayed for their ability to produce 3-HP from glycerol. The cells were grown on standard media supplemented with 6 μM of Coenzyme $B_{12}$, under anaerobic conditions in the absence of light (to protect the integrity of the Coenzyme $B_{12}$ necessary for DhaB activity). After 12 hours, IPTG was added to induce expression of the genes under the trc promoter at the same time 5 g/L of glycerol was added. After 12 more hours of anaerobic fermentation the fermentation broth was assayed for 3-HP by HPLC and GC, the plasmid, aldehyde dehydrogenase gene expressed and g/L of 3-HP measured were as follows: pSF17, aldA, 0.031; pPSF18 ALD4, 0.173; and pPSF19, ALDH2, 0.061. Cells expressing dhaB but no exogenous aldehyde dehydrogenase genes (plasmid pMH34) produced 0.015 g/L of 3-HP. Cells expressing aldA, ALD4, ALDH2 or aldB but not dhaB (plasmids pPFS13, pPFS14, pPFS15, pPFS16, respectively) all produced less then 0.005 g/L of 3-HP when the media the cells were growing in was supplemented with 2.5 g/L of 3-hydroxypropionaldehyde.

Other Hosts and Promoters

Applications of the 3-hydroxypropionic acid pathway such as the genetic constructs of the present invention can easily be expressed in other organisms. The required genes would need to be placed under control of an appropriate promoter or promoters. Some organism such as yeasts may require transcription terminators to be placed after each transcribed unit. The knowledge of the present intention makes such amendments possible. Such a genetic construct would need to be part of a vector that could either replicate in the new host or integrate into the chromosome of the new host. Many such vectors are commercially available for expression in gram-negative and gram-positive bacteria, yeast, mammalian cells, insect cell, plant, etc. For example, to express the 3-hydroxypropionic acid pathway in Rhodobacter capsulatus, one could obtain vector pNH2 from the American Type Culture Collection (ATTC). This is a shuttle vector for use in R. capsulatus and E. coli. Organisms such as Saccharomyces cerevisiae which can convert glucose to glycerol could be used as a host, such a construct would enable the production of 3-HP directly from glucose. Additionally, other substrates such as xylan could also be used given the selection of an appropriate host.

Stochiometric analysis shows that best stochiometric yield of 3-HP production in E. coli calculated on the basis of glucose consumed is obtained under aerobic conditions. Under aerobic condition $CO_2$ is the only carbon-containing co-product, in particular the generation of lactic acid which occurs under anaerobic conditions is avoided. Production of 3-HP under these conditions could result in a more economical recovery of 3-HP from the fermentation broth.

Alternatively, the dhaB gene and a gene encoding the appropriate aldehyde dehydrogenase could be cloned into the multiple cloning site of this vector in E. coli to facilitate construction, and then transformed into R. capsulatus. The R. capsulatus nifH promoter, provided on the plasmid, could be used to direct the transcription in R. capsulatus of the genes placed into pNF2 in series with one promoter, or with two copies of the nifH promoter. Expression of the genes in other organisms would require a procedure analogous to that presented here.

Alternative Aldehyde Dehydrogenases and Glycerol Dehydratases

Applications of the pathway for the production of 3-hydroxypropionic acid from glycerol can be made using other suitable aldehyde dehydrogenases. To be functional in this pathway an aldehyde dehydrogenase needs to be stable, readily expressed in the host of choice and have high enough activity towards 3-hydroxypropionaldehyde to enable it to make 3-HP. The knowledge of the present invention makes such amendments possible. A program of directed evolution could be undertaken to select for suitable aldehyde dehydrogenases or they could be recovered from native sources, the genes encoding these enzymes in conjunction with a gene encoding an appropriate glycerol dehydratase activity, would then be made part of any of the constructs envisioned here to produce 3-hydroxypropionic acid from glycerol.

A similar program of enzyme improvement including for example directed evolution could be carried out using the dhaB gene from Klebsiella pneumoniae as a starting point to obtain other variants of glycerol dehydratase that are superior in efficiency and stability to the form used in this invention. Alternatively, enzymes which catalyzes the same reaction may be isolated from others organisms and used in place of the Klebsiella pneumoniae glycerol dehydratase. Such enzymes may be especially useful in alternative hosts wherein they may be more readily expressed, be more stable and more efficient under the fermentation conditions best suited to the growth of the construct and the production and recovery of 3-HP.

---

What is claimed is:

1. A method for producing 3-hydroxypropionic acid comprising the steps of
   - providing in a fermenter a recombinant microorganism which carries a genetic construct which expresses the dhaB gene from *Klebsiella pneumoniae* and a gene for an aldehyde dehydrogenase, which are capable of catalyzing the production of 3-hydroxypropionic acid from glycerol;
   - providing a source of glycerol or glucose for the recombinant microorganism, and
   - fermenting the microorganism under conditions which result in the accumulation of 3-hydroxypropionic acid in solution in the fermenter.

2. A method for producing 3-hydroxypropionic acid comprising the steps of
   - providing in a fermenter a recombinant microorganism which carries a genetic construct which expresses the dhaB gene from *Klebsiella pneumoniae* and a gene for an aldehyde dehydrogenase, which are capable of catalyzing the production of 3-hydroxypropionic acid from glycerol;
   - providing a source of glycerol or glucose for the recombinant microorganism, and
   - fermenting the microorganism under conditions which result in the accumulation of 3-hydroxypropionic acid wherein the gene for the aldehyde dehydrogenase is selected from the group consisting of ALDH2, ALD4, aldA and aldB.

3. A method for producing 3-hydroxypropionic acid comprising the steps of
   - providing in a fermenter a recombinant microorganism which carries a genetic construct which expresses the dhaB gene from *Klebsiella pneumoniae* and a gene for an aldehyde dehydrogenase, which are capable of catalyzing the production of 3-hydroxypropionic acid from glycerol;
   - providing a source of glycerol or glucose for the recombinant microorganism, and
   - fermenting the microorganism under conditions which result in the accumulation of 3-hydroxypropionic acid wherein the aldehyde dehydrogenase selected from the group consisting of SEQ ID NO:2, SEQ ID NO:4, SEQ ID NO:6 and SEQ ID NO:8.

4. A recombinant *E. coli* host comprising in its inheritable genetic materials foreign dhaB gene from *Klebsiella pneumoniae* and a gene for aldehyde dehydrogenase, such that the host is capable of producing 3-hydroxypropionic acid from glycerol.

5. A recombinant *E. coli* host comprising in its inheritable genetic materials the dhaB gene from *Klebsiella pneumoniae* and the ald4 gene from *Saccharomycetes cervisiae*, such that the host is capable of producing 3-hydroxypropionic from glycerol.

6. A bacterial host comprising in its inheritable genetic material a genetic construction encoding for the expression of the dhaB gene from *Klebsiella pneumoniae* and an aldehyde dehydrogenase enzyme, such that the bacterial host is capable of converting glycerol to 3-hydroxypropionic acid.

7. A bacterial host comprising in its inheritable genetic material a genetic construction encoding on of a glycerol dehydratase enzyme, the amino acid sequence of which are selected from SEQ IDS NO:10, 11, 12 and 13, and an aldehyde dehydrogenase enzyme, such that the bacterial host is capable of converting glycerol to 3-hydroxypropionic acid wherein the aldehyde dehydrogenase is selected from the group consisting of SEQ ID NO:2, SEQ ID NO:4, SEQ ID NO:6 and SEQ ID NO:8.

8. A bacterial host comprising in its inheritable genetic material a genetic construction encoding for the expression of a glycerol dehydratase enzyme, the amino acid sequence of which are selected from SEQ IDS NO:10, 11, 12 and 13, and an aldehyde dehydrogenase enzyme, such that the bacterial host is capable of converting glycerol to 3-hydroxypropionic acid wherein the gene for the aldehyde dehydrogenase is selected from the group consisting of ALDH2, ALDA4, aldA and aldB.

* * * * *

SEQUENCE LISTING

<160> NUMBER OF SEQ ID NOS: 23

<210> SEQ ID NO 1
<211> LENGTH: 1529
<212> TYPE: DNA
<213> ORGANISM: Saccharomyces cerevisiae
<220> FEATURE:
<221> NAME/KEY: CDS
<222> LOCATION: (25)..(1509)

<400> SEQUENCE: 1

```
gtcgcggtac caaggaggta tcat atg tca cac ctt cct atg aca gtg cct        51
                           Met Ser His Leu Pro Met Thr Val Pro
                             1               5 atc aag ctg ccc aat ggg ttg gaa tat gag caa cca acg ggg ttg ttc        99
Ile Lys Leu Pro Asn Gly Leu Glu Tyr Glu Gln Pro Thr Gly Leu Phe
 10              15                  20                  25 atc aac aac aag ttt gtt cct tct aaa cag aac aag acc ttc gaa gtc       147
Ile Asn Asn Lys Phe Val Pro Ser Lys Gln Asn Lys Thr Phe Glu Val
                 30                  35                  40 att aac cct tcc acg gaa gaa gaa ata tgt cat att tat gaa ggt aga       195
Ile Asn Pro Ser Thr Glu Glu Glu Ile Cys His Ile Tyr Glu Gly Arg
             45                  50                  55 gag gac gat gtg gaa gag gcc gtg cag gcc gcc gac cgt gcc ttc tct       243
Glu Asp Asp Val Glu Glu Ala Val Gln Ala Ala Asp Arg Ala Phe Ser
         60                  65                  70 aat ggg tct tgg aac ggt atc gac cct att gac agg ggt aag gct ttg       291
Asn Gly Ser Trp Asn Gly Ile Asp Pro Ile Asp Arg Gly Lys Ala Leu
     75                  80                  85 tac agg tta gcc gaa tta att gaa cag gac aag gat gtc att gct tcc       339
Tyr Arg Leu Ala Glu Leu Ile Glu Gln Asp Lys Asp Val Ile Ala Ser
 90                  95                 100                 105 atc gag act ttg gat aac ggt aaa gct atc tct tcc tcg aga gga gat       387
Ile Glu Thr Leu Asp Asn Gly Lys Ala Ile Ser Ser Ser Arg Gly Asp
                110                 115                 120 gtt gat tta gtc atc aac tat ttg aaa tct tct gct ggc ttt gct gat       435
```

|   |   |   |   |   |   |   |   |   |   |   |   |   |   |   |   |      |
|---|---|---|---|---|---|---|---|---|---|---|---|---|---|---|---|------|
|   | Val | Asp | Leu | Val | Ile | Asn | Tyr | Leu | Lys | Ser | Ser | Ala | Gly | Phe | Ala | Asp |
|   |     |     | 125 |     |     |     | 130 |     |     |     |     | 135 |     |     |     |     |

```
aaa att gat ggt aga atg att gat act ggt aga acc cat ttt tct tac      483
Lys Ile Asp Gly Arg Met Ile Asp Thr Gly Arg Thr His Phe Ser Tyr
        140                 145                 150 act aag aga cag cct ttg ggt gtt tgt ggg cag att att cct tgg aat      531
Thr Lys Arg Gln Pro Leu Gly Val Cys Gly Gln Ile Ile Pro Trp Asn
    155                 160                 165 ttc cca ctg ttg atg tgg gcc tgg aag att gcc cct gct ttg gtc acc      579
Phe Pro Leu Leu Met Trp Ala Trp Lys Ile Ala Pro Ala Leu Val Thr
170                 175                 180                 185 ggt aac acc gtc gtg ttg aag act gcc gaa tcc acc cca ttg tcc gct      627
Gly Asn Thr Val Val Leu Lys Thr Ala Glu Ser Thr Pro Leu Ser Ala
                190                 195                 200 ttg tat gtg tct aaa tac atc cca cag gcg ggt att cca cct ggt gtg      675
Leu Tyr Val Ser Lys Tyr Ile Pro Gln Ala Gly Ile Pro Pro Gly Val
            205                 210                 215 atc aac att gta tcc ggg ttt ggt aag att gtg gtt gag gcc att aca      723
Ile Asn Ile Val Ser Gly Phe Gly Lys Ile Val Val Glu Ala Ile Thr
        220                 225                 230 aac cat cca aaa atc aaa aag gtt gcc ttc aca ggg tcc acg gct acg      771
Asn His Pro Lys Ile Lys Lys Val Ala Phe Thr Gly Ser Thr Ala Thr
235                 240                 245 ggt aga cac att tac cag tcc gca gcc gca ggc ttg aaa aaa gtg act      819
Gly Arg His Ile Tyr Gln Ser Ala Ala Ala Gly Leu Lys Lys Val Thr
250                 255                 260                 265 ttg gag ctg ggt ggt aaa tca cca aac att gtc ttc gcg gac gcc gag      867
Leu Glu Leu Gly Gly Lys Ser Pro Asn Ile Val Phe Ala Asp Ala Glu
                270                 275                 280 ttg aaa aaa gcc gtg caa aac att atc ctt ggt atc tac tac aat tct      915
Leu Lys Lys Ala Val Gln Asn Ile Ile Leu Gly Ile Tyr Tyr Asn Ser
            285                 290                 295 ggt gag gtc tgt tgt gcg ggt tca agg gtg tat gtt gaa gaa tct att      963
Gly Glu Val Cys Cys Ala Gly Ser Arg Val Tyr Val Glu Glu Ser Ile
        300                 305                 310 tac gac aaa ttc att gaa gag ttc aaa gcc gct tct gaa tcc atc aag     1011
Tyr Asp Lys Phe Ile Glu Glu Phe Lys Ala Ala Ser Glu Ser Ile Lys
315                 320                 325 gtg ggc gac cca ttc gat gaa tct act ttc caa ggt gca caa acc tct     1059
Val Gly Asp Pro Phe Asp Glu Ser Thr Phe Gln Gly Ala Gln Thr Ser
330                 335                 340                 345 caa atg caa cta aac aaa atc ttg aaa tac gtt gac att ggt aag aat     1107
Gln Met Gln Leu Asn Lys Ile Leu Lys Tyr Val Asp Ile Gly Lys Asn
                350                 355                 360 gaa ggt gct act ttg att acc ggt ggt gaa aga tta ggt agc aag ggt     1155
Glu Gly Ala Thr Leu Ile Thr Gly Gly Glu Arg Leu Gly Ser Lys Gly
            365                 370                 375 tac ttc att aag cca act gtc ttt ggt gac gtt aag gaa gac atg aga     1203
Tyr Phe Ile Lys Pro Thr Val Phe Gly Asp Val Lys Glu Asp Met Arg
        380                 385                 390 att gtc aaa gag gaa atc ttt ggc cct gtt gtc act gta acc aaa ttc     1251
Ile Val Lys Glu Glu Ile Phe Gly Pro Val Val Thr Val Thr Lys Phe
395                 400                 405 aaa tct gcc gac gaa gtc att aac atg gcg aac gat tct gaa tac ggg     1299
Lys Ser Ala Asp Glu Val Ile Asn Met Ala Asn Asp Ser Glu Tyr Gly
410                 415                 420                 425 ttg gct gct ggt att cac acc tct aat att aat acc gcc tta aaa gtg     1347
Leu Ala Ala Gly Ile His Thr Ser Asn Ile Asn Thr Ala Leu Lys Val
                430                 435                 440
```

```
gct gat aga gtt aat gcg ggt acg gtc tgg ata aac act tat aac gat    1395
Ala Asp Arg Val Asn Ala Gly Thr Val Trp Ile Asn Thr Tyr Asn Asp
            445                 450                 455 ttc cac cac gca gtt cct ttc ggg ggg ttc aat gca tct ggt ttg ggc    1443
Phe His His Ala Val Pro Phe Gly Gly Phe Asn Ala Ser Gly Leu Gly
        460                 465                 470 agg gaa atg tct gtt gat gct tta caa aac tac ttg caa gtt aaa gcg    1491
Arg Glu Met Ser Val Asp Ala Leu Gln Asn Tyr Leu Gln Val Lys Ala
475                 480                 485 gtc cgt gcc aaa ttg gac gagtaagagc tcgaattcgc                      1529
Val Arg Ala Lys Leu Asp
490             495

<210> SEQ ID NO 2
<211> LENGTH: 495
<212> TYPE: PRT
<213> ORGANISM: Saccharomyces cerevisiae

<400> SEQUENCE: 2

Met Ser His Leu Pro Met Thr Val Pro Ile Lys Leu Pro Asn Gly Leu
 1               5                  10                  15

Glu Tyr Glu Gln Pro Thr Gly Leu Phe Ile Asn Asn Lys Phe Val Pro
            20                  25                  30

Ser Lys Gln Asn Lys Thr Phe Glu Val Ile Asn Pro Ser Thr Glu Glu
        35                  40                  45

Glu Ile Cys His Ile Tyr Glu Gly Arg Glu Asp Asp Val Glu Glu Ala
    50                  55                  60

Val Gln Ala Ala Asp Arg Ala Phe Ser Asn Gly Ser Trp Asn Gly Ile
65                  70                  75                  80

Asp Pro Ile Asp Arg Gly Lys Ala Leu Tyr Arg Leu Ala Glu Leu Ile
                85                  90                  95

Glu Gln Asp Lys Asp Val Ile Ala Ser Ile Glu Thr Leu Asp Asn Gly
            100                 105                 110

Lys Ala Ile Ser Ser Ser Arg Gly Asp Val Asp Leu Val Ile Asn Tyr
        115                 120                 125

Leu Lys Ser Ser Ala Gly Phe Ala Asp Lys Ile Asp Gly Arg Met Ile
    130                 135                 140

Asp Thr Gly Arg Thr His Phe Ser Tyr Thr Lys Arg Gln Pro Leu Gly
145                 150                 155                 160

Val Cys Gly Gln Ile Ile Pro Trp Asn Phe Pro Leu Leu Met Trp Ala
                165                 170                 175

Trp Lys Ile Ala Pro Ala Leu Val Thr Gly Asn Thr Val Val Leu Lys
            180                 185                 190

Thr Ala Glu Ser Thr Pro Leu Ser Ala Leu Tyr Val Ser Lys Tyr Ile
        195                 200                 205

Pro Gln Ala Gly Ile Pro Pro Gly Val Ile Asn Ile Val Ser Gly Phe
    210                 215                 220

Gly Lys Ile Val Val Glu Ala Ile Thr Asn His Pro Lys Ile Lys Lys
225                 230                 235                 240

Val Ala Phe Thr Gly Ser Thr Ala Thr Gly Arg His Ile Tyr Gln Ser
                245                 250                 255

Ala Ala Ala Gly Leu Lys Lys Val Thr Leu Glu Leu Gly Gly Lys Ser
            260                 265                 270

Pro Asn Ile Val Phe Ala Asp Ala Glu Leu Lys Lys Ala Val Gln Asn
        275                 280                 285

Ile Ile Leu Gly Ile Tyr Tyr Asn Ser Gly Glu Val Cys Cys Ala Gly
```

-continued

```
                290                 295                 300
Ser Arg Val Tyr Val Glu Glu Ser Ile Tyr Asp Lys Phe Ile Glu
305                 310                 315                 320

Phe Lys Ala Ala Ser Glu Ser Ile Lys Val Gly Asp Pro Phe Asp Glu
                325                 330                 335

Ser Thr Phe Gln Gly Ala Gln Thr Ser Gln Met Gln Leu Asn Lys Ile
                340                 345                 350

Leu Lys Tyr Val Asp Ile Gly Lys Asn Glu Gly Ala Thr Leu Ile Thr
                355                 360                 365

Gly Gly Glu Arg Leu Gly Ser Lys Gly Tyr Phe Ile Lys Pro Thr Val
370                 375                 380

Phe Gly Asp Val Lys Glu Asp Met Arg Ile Val Lys Glu Ile Phe
385                 390                 395                 400

Gly Pro Val Val Thr Val Thr Lys Phe Lys Ser Ala Asp Glu Val Ile
                405                 410                 415

Asn Met Ala Asn Asp Ser Glu Tyr Gly Leu Ala Ala Gly Ile His Thr
                420                 425                 430

Ser Asn Ile Asn Thr Ala Leu Lys Val Ala Asp Arg Val Asn Ala Gly
                435                 440                 445

Thr Val Trp Ile Asn Thr Tyr Asn Asp Phe His His Ala Val Pro Phe
450                 455                 460

Gly Gly Phe Asn Ala Ser Gly Leu Gly Arg Glu Met Ser Val Asp Ala
465                 470                 475                 480

Leu Gln Asn Tyr Leu Gln Val Lys Ala Val Arg Ala Lys Leu Asp
                485                 490                 495

<210> SEQ ID NO 3
<211> LENGTH: 1541
<212> TYPE: DNA
<213> ORGANISM: Homo sapiens
<220> FEATURE:
<221> NAME/KEY: CDS
<222> LOCATION: (22)..(1521)

<400> SEQUENCE: 3
gcggtaccaa ggagatatca t atg tca gcc gcc gcc acc cag gcc gtg cct         51
                         Met Ser Ala Ala Ala Thr Gln Ala Val Pro
                           1               5                  10 gcc ccc aac cag cag ccc gag gtc ttc tgc aac cag att ttc ata aac        99
Ala Pro Asn Gln Gln Pro Glu Val Phe Cys Asn Gln Ile Phe Ile Asn
                 15                  20                  25 aat gaa tgg cac gat gcc gtc agc agg aaa aca ttc ccc acc gtc aat       147
Asn Glu Trp His Asp Ala Val Ser Arg Lys Thr Phe Pro Thr Val Asn
             30                  35                  40 ccg tcc act gga gag gtc atc tgt cag gta gct gaa ggg gac aag gaa       195
Pro Ser Thr Gly Glu Val Ile Cys Gln Val Ala Glu Gly Asp Lys Glu
         45                  50                  55 gat gtg gac aag gca cgt gaa ggc cgc ccg ggc gcc ttc cag ctg ggc       243
Asp Val Asp Lys Ala Arg Glu Gly Arg Pro Gly Ala Phe Gln Leu Gly
     60                  65                  70 tca cct tgg cgc cgc atg gac gca tca cac agc ggc cgg ctg ctg aac       291
Ser Pro Trp Arg Arg Met Asp Ala Ser His Ser Gly Arg Leu Leu Asn
 75                  80                  85                  90 cgc ctg gcc gat ctg atc gag cgg gac cgg acc tac ctg gcg gcc ttg       339
Arg Leu Ala Asp Leu Ile Glu Arg Asp Arg Thr Tyr Leu Ala Ala Leu
                 95                 100                 105 gag acc ctg gac aat ggc aag ccc tat gtc atc tcc tac ctg gtg gat       387
Glu Thr Leu Asp Asn Gly Lys Pro Tyr Val Ile Ser Tyr Leu Val Asp
```

```
                    110                 115                 120
ttg gac atg gtc ctc aaa tgt ctc cgg tat tat gcc ggc tgg gct gat    435
Leu Asp Met Val Leu Lys Cys Leu Arg Tyr Tyr Ala Gly Trp Ala Asp
        125                 130                 135 aag tac cac ggg aaa acc atc ccc att gac gga gac ttc ttc agc tac    483
Lys Tyr His Gly Lys Thr Ile Pro Ile Asp Gly Asp Phe Phe Ser Tyr
    140                 145                 150 aca cgc cat gaa cct gtg ggg gtg tgc ggg cag atc att ccg tgg aat    531
Thr Arg His Glu Pro Val Gly Val Cys Gly Gln Ile Ile Pro Trp Asn
155                 160                 165                 170 ttc ccg ctc ctg atg caa gca tgg aag ctg ggc cca gcc ttg gca act    579
Phe Pro Leu Leu Met Gln Ala Trp Lys Leu Gly Pro Ala Leu Ala Thr
                175                 180                 185 gga aac gtg gtt gtg atg aag gta gct gag cag aca ccc ctc acc gcc    627
Gly Asn Val Val Val Met Lys Val Ala Glu Gln Thr Pro Leu Thr Ala
            190                 195                 200 ctc tat gtg gcc aac ctg atc aag gag gct ggc ttt ccc cct ggt gtg    675
Leu Tyr Val Ala Asn Leu Ile Lys Glu Ala Gly Phe Pro Pro Gly Val
        205                 210                 215 gtc aac att gtg cct gga ttt ggc ccc acg gct ggg gcc gcc att gcc    723
Val Asn Ile Val Pro Gly Phe Gly Pro Thr Ala Gly Ala Ala Ile Ala
    220                 225                 230 tcc cat gag gat gtg gac aaa gtg gca ttc aca ggc tcc act gag att    771
Ser His Glu Asp Val Asp Lys Val Ala Phe Thr Gly Ser Thr Glu Ile
235                 240                 245                 250 ggc cgc gta atc cag gtt gct gct ggg agc agc aac ctc aag aga gtg    819
Gly Arg Val Ile Gln Val Ala Ala Gly Ser Ser Asn Leu Lys Arg Val
                255                 260                 265 acc ttg gag ctg ggg ggg aag agc ccc aac atc atc atg tca gat gcc    867
Thr Leu Glu Leu Gly Gly Lys Ser Pro Asn Ile Ile Met Ser Asp Ala
            270                 275                 280 gat atg gat tgg gcc gtg gaa cag gcc cac ttc gcc ctg ttc ttc aac    915
Asp Met Asp Trp Ala Val Glu Gln Ala His Phe Ala Leu Phe Phe Asn
        285                 290                 295 cag ggc cag tgc tgc tgt gcc ggc tcc cgg acc ttc gtg cag gag gac    963
Gln Gly Gln Cys Cys Cys Ala Gly Ser Arg Thr Phe Val Gln Glu Asp
    300                 305                 310 atc tat gat gag ttt gtg gtg cgg agc gtt gcc cgg gcc aag tct cgg   1011
Ile Tyr Asp Glu Phe Val Val Arg Ser Val Ala Arg Ala Lys Ser Arg
315                 320                 325                 330 gtg gtc ggg aac ccc ttt gat agc aag acc gag cag ggg ccg cag gtg   1059
Val Val Gly Asn Pro Phe Asp Ser Lys Thr Glu Gln Gly Pro Gln Val
                335                 340                 345 gat gaa act cag ttt aag aag atc ctc ggc tac atc aac acg ggg aag   1107
Asp Glu Thr Gln Phe Lys Lys Ile Leu Gly Tyr Ile Asn Thr Gly Lys
            350                 355                 360 caa gag ggg gcg aag ctg ctg tgt ggt ggg ggc att gct gct gac cgt   1155
Gln Glu Gly Ala Lys Leu Leu Cys Gly Gly Gly Ile Ala Ala Asp Arg
        365                 370                 375 ggt tac ttc atc cag ccc act gtg ttt gga gat gtg cag gat ggc atg   1203
Gly Tyr Phe Ile Gln Pro Thr Val Phe Gly Asp Val Gln Asp Gly Met
    380                 385                 390 acc atc gcc aag gag gag atc ttc ggg cca gtg atg cag atc ctg aag   1251
Thr Ile Ala Lys Glu Glu Ile Phe Gly Pro Val Met Gln Ile Leu Lys
395                 400                 405                 410 ttc aag acc ata gag gag gtt gtt ggg aga gcc aac aat tcc acg tac   1299
Phe Lys Thr Ile Glu Glu Val Val Gly Arg Ala Asn Asn Ser Thr Tyr
                415                 420                 425 ggg ctg gcc gca gct gtc ttc aca aag gat ttg gac aag gcc aat tac   1347
```

-continued

```
Gly Leu Ala Ala Ala Val Phe Thr Lys Asp Leu Asp Lys Ala Asn Tyr
                430                 435                 440 ctg tcc cag gcc ctc cag gcg ggc act gtg tgg gtc aac tgc tat gat        1395
Leu Ser Gln Ala Leu Gln Ala Gly Thr Val Trp Val Asn Cys Tyr Asp
            445                 450                 455 gtg ttt gga gcc cag tca ccc ttt ggt ggc tac aag atg tcg ggg agt        1443
Val Phe Gly Ala Gln Ser Pro Phe Gly Gly Tyr Lys Met Ser Gly Ser
    460                 465                 470 ggc cgg gag ttg ggc gag tac ggg ctg cag gca tac act gaa gtg aaa        1491
Gly Arg Glu Leu Gly Glu Tyr Gly Leu Gln Ala Tyr Thr Glu Val Lys
475                 480                 485                 490 act gtc aca gtc aaa gtg cct cag aag aac tcataagagc tcgaattcgc          1541
Thr Val Thr Val Lys Val Pro Gln Lys Asn
                495                 500
```

<210> SEQ ID NO 4
<211> LENGTH: 500
<212> TYPE: PRT
<213> ORGANISM: Homo sapiens

<400> SEQUENCE: 4

```
Met Ser Ala Ala Ala Thr Gln Ala Val Pro Ala Pro Asn Gln Gln Pro
  1               5                  10                  15

Glu Val Phe Cys Asn Gln Ile Phe Ile Asn Asn Glu Trp His Asp Ala
                 20                  25                  30

Val Ser Arg Lys Thr Phe Pro Thr Val Asn Pro Ser Thr Gly Glu Val
             35                  40                  45

Ile Cys Gln Val Ala Glu Gly Asp Lys Glu Asp Val Asp Lys Ala Arg
         50                  55                  60

Glu Gly Arg Pro Gly Ala Phe Gln Leu Gly Ser Pro Trp Arg Arg Met
 65                  70                  75                  80

Asp Ala Ser His Ser Gly Arg Leu Leu Asn Arg Leu Ala Asp Leu Ile
                 85                  90                  95

Glu Arg Asp Arg Thr Tyr Leu Ala Ala Leu Glu Thr Leu Asp Asn Gly
            100                 105                 110

Lys Pro Tyr Val Ile Ser Tyr Leu Val Asp Leu Asp Met Val Leu Lys
        115                 120                 125

Cys Leu Arg Tyr Tyr Ala Gly Trp Ala Asp Lys Tyr His Gly Lys Thr
    130                 135                 140

Ile Pro Ile Asp Gly Asp Phe Phe Ser Tyr Thr Arg His Glu Pro Val
145                 150                 155                 160

Gly Val Cys Gly Gln Ile Ile Pro Trp Asn Phe Pro Leu Leu Met Gln
                165                 170                 175

Ala Trp Lys Leu Gly Pro Ala Leu Ala Thr Gly Asn Val Val Val Met
            180                 185                 190

Lys Val Ala Glu Gln Thr Pro Leu Thr Ala Leu Tyr Val Ala Asn Leu
        195                 200                 205

Ile Lys Glu Ala Gly Phe Pro Pro Gly Val Val Asn Ile Val Pro Gly
    210                 215                 220

Phe Gly Pro Thr Ala Gly Ala Ala Ile Ala Ser His Glu Asp Val Asp
225                 230                 235                 240

Lys Val Ala Phe Thr Gly Ser Thr Glu Ile Gly Arg Val Ile Gln Val
                245                 250                 255

Ala Ala Gly Ser Ser Asn Leu Lys Arg Val Thr Leu Glu Leu Gly Gly
            260                 265                 270

Lys Ser Pro Asn Ile Ile Met Ser Asp Ala Asp Met Asp Trp Ala Val
```

```
                    275                 280                 285
Glu Gln Ala His Phe Ala Leu Phe Phe Asn Gln Gly Gln Cys Cys Cys
    290                 295                 300
Ala Gly Ser Arg Thr Phe Val Gln Glu Asp Ile Tyr Asp Glu Phe Val
305                 310                 315                 320
Val Arg Ser Val Ala Arg Ala Lys Ser Arg Val Val Gly Asn Pro Phe
                325                 330                 335
Asp Ser Lys Thr Glu Gln Gly Pro Gln Val Asp Glu Thr Gln Phe Lys
            340                 345                 350
Lys Ile Leu Gly Tyr Ile Asn Thr Gly Lys Gln Glu Gly Ala Lys Leu
                355                 360                 365
Leu Cys Gly Gly Ile Ala Ala Asp Arg Gly Tyr Phe Ile Gln Pro
    370                 375                 380
Thr Val Phe Gly Asp Val Gln Asp Gly Met Thr Ile Ala Lys Glu Glu
385                 390                 395                 400
Ile Phe Gly Pro Val Met Gln Ile Leu Lys Phe Lys Thr Ile Glu Glu
                405                 410                 415
Val Val Gly Arg Ala Asn Asn Ser Thr Tyr Gly Leu Ala Ala Ala Val
                420                 425                 430
Phe Thr Lys Asp Leu Asp Lys Ala Asn Tyr Leu Ser Gln Ala Leu Gln
            435                 440                 445
Ala Gly Thr Val Trp Val Asn Cys Tyr Asp Val Phe Gly Ala Gln Ser
    450                 455                 460
Pro Phe Gly Gly Tyr Lys Met Ser Gly Ser Gly Arg Glu Leu Gly Glu
465                 470                 475                 480
Tyr Gly Leu Gln Ala Tyr Thr Glu Val Lys Thr Val Thr Val Lys Val
                485                 490                 495
Pro Gln Lys Asn
            500

<210> SEQ ID NO 5
<211> LENGTH: 1513
<212> TYPE: DNA
<213> ORGANISM: Escherichia coli
<220> FEATURE:
<221> NAME/KEY: CDS
<222> LOCATION: (37)..(1473)

<400> SEQUENCE: 5
gctaccatgg cttaaccggt accaaggaga tatcat atg tca gta ccc gtt caa        54
                                       Met Ser Val Pro Val Gln
                                         1               5 cat cct atg tat atc gat gga cag ttt gtt acc tgg cgt gga gac gca       102
His Pro Met Tyr Ile Asp Gly Gln Phe Val Thr Trp Arg Gly Asp Ala
            10                  15                  20 tgg att gat gtg gta aac cct gct aca gag gct gtc att tcc cgc ata       150
Trp Ile Asp Val Val Asn Pro Ala Thr Glu Ala Val Ile Ser Arg Ile
        25                  30                  35 ccc gat ggt cag gcc gag gat gcc cgt aag gca atc gat gca gca gaa       198
Pro Asp Gly Gln Ala Glu Asp Ala Arg Lys Ala Ile Asp Ala Ala Glu
    40                  45                  50 cgt gca caa cca gaa tgg gaa gcg ttg cct gct att gaa cgc gcc agt       246
Arg Ala Gln Pro Glu Trp Glu Ala Leu Pro Ala Ile Glu Arg Ala Ser
55                  60                  65                  70 tgg ttg cgc aaa atc tcc gcc ggg atc cgc gaa cgc gcc agt gaa atc       294
Trp Leu Arg Lys Ile Ser Ala Gly Ile Arg Glu Arg Ala Ser Glu Ile
                75                  80                  85
```

```
                                                             -continued agt gcg ctg att gtt gaa gaa ggg ggc aag atc cag cag ctg gct gaa        342
Ser Ala Leu Ile Val Glu Glu Gly Gly Lys Ile Gln Gln Leu Ala Glu
            90                  95                 100 gtc gaa gtg gct ttt act gcc gac tat atc gat tac atg gcg gag tgg        390
Val Glu Val Ala Phe Thr Ala Asp Tyr Ile Asp Tyr Met Ala Glu Trp
    105                 110                 115 gca cgg cgt tac gag ggc gag att att caa agc gat cgt cca gga gaa        438
Ala Arg Arg Tyr Glu Gly Glu Ile Ile Gln Ser Asp Arg Pro Gly Glu
        120                 125                 130 aat att ctt ttg ttt aaa cgt gcg ctt ggt gtg act acc ggc att ctg        486
Asn Ile Leu Leu Phe Lys Arg Ala Leu Gly Val Thr Thr Gly Ile Leu
135                 140                 145                 150 ccg tgg aac ttc ccg ttc ttc ctc att gcc cgc aaa atg gct ccc gct        534
Pro Trp Asn Phe Pro Phe Phe Leu Ile Ala Arg Lys Met Ala Pro Ala
                155                 160                 165 ctt ttg acc ggt aat acc atc gtc att aaa cct agt gaa ttt acg aca        582
Leu Leu Thr Gly Asn Thr Ile Val Ile Lys Pro Ser Glu Phe Thr Thr
            170                 175                 180 aac aat gcg att gca ttc gcc aaa atc gtc gat gaa ata ggc ctt ccg        630
Asn Asn Ala Ile Ala Phe Ala Lys Ile Val Asp Glu Ile Gly Leu Pro
    185                 190                 195 cgc ggc gtg ttt aac ctt gta ctg ggg cgt ggt gaa acc gtt ggg caa        678
Arg Gly Val Phe Asn Leu Val Leu Gly Arg Gly Glu Thr Val Gly Gln
        200                 205                 210 gaa ctg gcg ggt aac cca aag gtc gca atg gtc agt atg aca ggc agc        726
Glu Leu Ala Gly Asn Pro Lys Val Ala Met Val Ser Met Thr Gly Ser
215                 220                 225                 230 gtc tct gca ggt gag aag atc atg gcg act gcg gcg aaa aac atc acc        774
Val Ser Ala Gly Glu Lys Ile Met Ala Thr Ala Ala Lys Asn Ile Thr
                235                 240                 245 aaa gtg tgt ctg gaa ttg ggg ggt aaa gca cca gct atc gta atg gac        822
Lys Val Cys Leu Glu Leu Gly Gly Lys Ala Pro Ala Ile Val Met Asp
            250                 255                 260 gat gcc gat ctt gaa ctg gca gtc aaa gcc atc gtt gat tca cgc gtc        870
Asp Ala Asp Leu Glu Leu Ala Val Lys Ala Ile Val Asp Ser Arg Val
    265                 270                 275 att aat agt ggg caa gtg tgt aac tgt gca gaa cgt gtt tat gta cag        918
Ile Asn Ser Gly Gln Val Cys Asn Cys Ala Glu Arg Val Tyr Val Gln
        280                 285                 290 aaa ggc att tat gat cag ttc gtc aat cgg ctg ggt gaa gcg atg cag        966
Lys Gly Ile Tyr Asp Gln Phe Val Asn Arg Leu Gly Glu Ala Met Gln
295                 300                 305                 310 gcg gtt caa ttt ggt aac ccc gct gaa cgc aac gac att gcg atg ggg       1014
Ala Val Gln Phe Gly Asn Pro Ala Glu Arg Asn Asp Ile Ala Met Gly
                315                 320                 325 ccg ttg att aac gcc gcg gcg ctg gaa agg gtc gag caa aaa gtg gcg       1062
Pro Leu Ile Asn Ala Ala Ala Leu Glu Arg Val Glu Gln Lys Val Ala
            330                 335                 340 cgc gca gta gaa gaa ggg gcg aga gtg gcg ttc ggt ggc aaa gcg gta       1110
Arg Ala Val Glu Glu Gly Ala Arg Val Ala Phe Gly Gly Lys Ala Val
    345                 350                 355 gag ggg aaa gga tat tat tat ccg ccg aca ttg ctg ctg gat gtt cgc       1158
Glu Gly Lys Gly Tyr Tyr Tyr Pro Pro Thr Leu Leu Leu Asp Val Arg
        360                 365                 370 cag gaa atg tcg att atg cat gag gaa acc ttt ggc ccg gtg ctg cca       1206
Gln Glu Met Ser Ile Met His Glu Glu Thr Phe Gly Pro Val Leu Pro
375                 380                 385                 390 gtt gtc gca ttt gac acg ctg gaa gat gct atc tca atg gct aat gac       1254
Val Val Ala Phe Asp Thr Leu Glu Asp Ala Ile Ser Met Ala Asn Asp
                395                 400                 405
```

-continued

| | |
|---|---|
| agt gat tac ggc ctg acc tca tca atc tat acc caa aat ctg aac gtc<br>Ser Asp Tyr Gly Leu Thr Ser Ser Ile Tyr Thr Gln Asn Leu Asn Val<br>410                             415                          420 | 1302 |
| gcg atg aaa gcc att aaa ggg ctg aag ttt ggt gaa act tac atc aac<br>Ala Met Lys Ala Ile Lys Gly Leu Lys Phe Gly Glu Thr Tyr Ile Asn<br>        425                           430                          435 | 1350 |
| cgt gaa aac ttc gaa gct atg caa ggc ttc cac gcc gga tgg cgt aaa<br>Arg Glu Asn Phe Glu Ala Met Gln Gly Phe His Ala Gly Trp Arg Lys<br>440                             445                         450 | 1398 |
| tcc ggt att ggc ggc gca gat ggt aaa cat ggc ttg cat gga tat ctg<br>Ser Gly Ile Gly Gly Ala Asp Gly Lys His Gly Leu His Gly Tyr Leu<br>455                        460                        465                          470 | 1446 |
| cag acc cag gtg gtt tat tta cag tct taagagctcg aattcccgtc<br>Gln Thr Gln Val Val Tyr Leu Gln Ser<br>                  475 | 1493 |
| gacggctcta gactcgagcg | 1513 |

<210> SEQ ID NO 6
<211> LENGTH: 479
<212> TYPE: PRT
<213> ORGANISM: Escherichia coli

<400> SEQUENCE: 6

Met Ser Val Pro Val Gln His Pro Met Tyr Ile Asp Gly Gln Phe Val
1                 5                     10                     15

Thr Trp Arg Gly Asp Ala Trp Ile Asp Val Val Asn Pro Ala Thr Glu
                 20                     25                     30

Ala Val Ile Ser Arg Ile Pro Asp Gly Gln Ala Glu Asp Ala Arg Lys
              35                     40                     45

Ala Ile Asp Ala Ala Glu Arg Ala Gln Pro Glu Trp Glu Ala Leu Pro
        50                     55                     60

Ala Ile Glu Arg Ala Ser Trp Leu Arg Lys Ile Ser Ala Gly Ile Arg
65                 70                     75                     80

Glu Arg Ala Ser Glu Ile Ser Ala Leu Ile Val Glu Glu Gly Gly Lys
                 85                     90                     95

Ile Gln Gln Leu Ala Glu Val Glu Val Ala Phe Thr Ala Asp Tyr Ile
              100                     105                    110

Asp Tyr Met Ala Glu Trp Ala Arg Arg Tyr Glu Gly Glu Ile Ile Gln
            115                    120                    125

Ser Asp Arg Pro Gly Glu Asn Ile Leu Leu Phe Lys Arg Ala Leu Gly
        130                     135                    140

Val Thr Thr Gly Ile Leu Pro Trp Asn Phe Pro Phe Phe Leu Ile Ala
145               150                    155                    160

Arg Lys Met Ala Pro Ala Leu Leu Thr Gly Asn Thr Ile Val Ile Lys
                 165                     170                    175

Pro Ser Glu Phe Thr Thr Asn Asn Ala Ile Ala Phe Ala Lys Ile Val
            180                    185                    190

Asp Glu Ile Gly Leu Pro Arg Gly Val Phe Asn Leu Val Leu Gly Arg
        195                     200                    205

Gly Glu Thr Val Gly Gln Glu Leu Ala Gly Asn Pro Lys Val Ala Met
        210                     215                    220

Val Ser Met Thr Gly Ser Val Ser Ala Gly Glu Lys Ile Met Ala Thr
225               230                    235                    240

Ala Ala Lys Asn Ile Thr Lys Val Cys Leu Glu Leu Gly Gly Lys Ala
                 245                     250                    255

-continued

```
Pro Ala Ile Val Met Asp Asp Ala Asp Leu Glu Leu Ala Val Lys Ala
            260                 265                 270

Ile Val Asp Ser Arg Val Ile Asn Ser Gly Gln Val Cys Asn Cys Ala
        275                 280                 285

Glu Arg Val Tyr Val Gln Lys Gly Ile Tyr Asp Gln Phe Val Asn Arg
    290                 295                 300

Leu Gly Glu Ala Met Gln Ala Val Gln Phe Gly Asn Pro Ala Glu Arg
305                 310                 315                 320

Asn Asp Ile Ala Met Gly Pro Leu Ile Asn Ala Ala Leu Glu Arg
                325                 330                 335

Val Glu Gln Lys Val Ala Arg Ala Val Glu Gly Ala Arg Val Ala
            340                 345                 350

Phe Gly Gly Lys Ala Val Glu Gly Lys Gly Tyr Tyr Tyr Pro Pro Thr
                355                 360                 365

Leu Leu Leu Asp Val Arg Gln Glu Met Ser Ile Met His Glu Thr
    370                 375                 380

Phe Gly Pro Val Leu Pro Val Val Ala Phe Asp Thr Leu Glu Asp Ala
385                 390                 395                 400

Ile Ser Met Ala Asn Asp Ser Asp Tyr Gly Leu Thr Ser Ser Ile Tyr
                405                 410                 415

Thr Gln Asn Leu Asn Val Ala Met Lys Ala Ile Lys Gly Leu Lys Phe
            420                 425                 430

Gly Glu Thr Tyr Ile Asn Arg Glu Asn Phe Glu Ala Met Gln Gly Phe
                435                 440                 445

His Ala Gly Trp Arg Lys Ser Gly Ile Gly Gly Ala Asp Gly Lys His
    450                 455                 460

Gly Leu His Gly Tyr Leu Gln Thr Gln Val Val Tyr Leu Gln Ser
465                 470                 475
```

<210> SEQ ID NO 7
<211> LENGTH: 1574
<212> TYPE: DNA
<213> ORGANISM: Escherichia coli
<220> FEATURE:
<221> NAME/KEY: CDS
<222> LOCATION: (22)..(1557)

<400> SEQUENCE: 7

```
gcggtaccaa ggaggtatca t atg acc aat aat ccc cct tca gca cag att        51
                        Met Thr Asn Asn Pro Pro Ser Ala Gln Ile
                          1               5                  10 aag ccc ggc gag tat ggt ttc ccc ctc aag tta aaa gcc cgc tat gac        99
Lys Pro Gly Glu Tyr Gly Phe Pro Leu Lys Leu Lys Ala Arg Tyr Asp
                 15                  20                  25 aac ttt att ggc ggc gaa tgg gta gcc cct gcc gac ggc gag tat tac       147
Asn Phe Ile Gly Gly Glu Trp Val Ala Pro Ala Asp Gly Glu Tyr Tyr
             30                  35                  40 cag aat ctg acg ccg gtg acc ggg cag ctg ctg tgc gaa gtg gcg tct       195
Gln Asn Leu Thr Pro Val Thr Gly Gln Leu Leu Cys Glu Val Ala Ser
         45                  50                  55 tcg ggc aaa cga gac atc gat ctg gcg ctg gat gct gcg cac aaa gtg       243
Ser Gly Lys Arg Asp Ile Asp Leu Ala Leu Asp Ala Ala His Lys Val
     60                  65                  70 aaa gat aaa tgg gcg cac acc tcg gtg cag gat cgt gcg gcg att ctg       291
Lys Asp Lys Trp Ala His Thr Ser Val Gln Asp Arg Ala Ala Ile Leu
 75                  80                  85                  90 ttt aag att gcc gat cga atg gaa caa aac ctc gag ctg tta gcg aca       339
Phe Lys Ile Ala Asp Arg Met Glu Gln Asn Leu Glu Leu Leu Ala Thr
```

-continued

```
                 95                  100                 105
gct gaa acc tgg gat aac ggc aaa ccc att cgc gaa acc agt gct gcg        387
Ala Glu Thr Trp Asp Asn Gly Lys Pro Ile Arg Glu Thr Ser Ala Ala
            110                 115                 120 gat gta ccg ctg gcg att gac cat ttc cgc tat ttc gcc tcg tgt att        435
Asp Val Pro Leu Ala Ile Asp His Phe Arg Tyr Phe Ala Ser Cys Ile
        125                 130                 135 cgg gcg cag gaa ggt ggg atc agt gaa gtt gat agc gaa acc gtg gcc        483
Arg Ala Gln Glu Gly Gly Ile Ser Glu Val Asp Ser Glu Thr Val Ala
    140                 145                 150 tat cat ttc cat gaa ccg tta ggc gtg gtg ggg cag att atc ccg tgg        531
Tyr His Phe His Glu Pro Leu Gly Val Val Gly Gln Ile Ile Pro Trp
155                 160                 165                 170 aac ttc ccg ctg ctg atg gcg agc tgg aaa atg gct ccc gcg ctg gcg        579
Asn Phe Pro Leu Leu Met Ala Ser Trp Lys Met Ala Pro Ala Leu Ala
                175                 180                 185 gcg ggc aac tgt gtg gtg ctg aaa ccc gca cgt ctt acc ccg ctt tct        627
Ala Gly Asn Cys Val Val Leu Lys Pro Ala Arg Leu Thr Pro Leu Ser
            190                 195                 200 gta ctg ctg cta atg gaa att gtc ggt gat tta ctg ccg ccg ggc gtg        675
Val Leu Leu Leu Met Glu Ile Val Gly Asp Leu Leu Pro Pro Gly Val
        205                 210                 215 gtg aac gtg gtc aat ggc gca ggt ggg gta att ggc gaa tat ctg gcg        723
Val Asn Val Val Asn Gly Ala Gly Gly Val Ile Gly Glu Tyr Leu Ala
    220                 225                 230 acc tcg aaa cgc atc gcc aaa gtg gcg ttt acc ggc tca acg gaa gtg        771
Thr Ser Lys Arg Ile Ala Lys Val Ala Phe Thr Gly Ser Thr Glu Val
235                 240                 245                 250 ggc caa caa att atg caa tac gca acg caa aac att att ccg gtg acg        819
Gly Gln Gln Ile Met Gln Tyr Ala Thr Gln Asn Ile Ile Pro Val Thr
                255                 260                 265 ctg gag ttg ggc ggt aag tcg cca aat atc gtc ttt gct gat gtg atg        867
Leu Glu Leu Gly Gly Lys Ser Pro Asn Ile Val Phe Ala Asp Val Met
            270                 275                 280 gat gaa gaa gat gcc ttt ttc gat aaa gcg ctg gaa ggc ttt gca ctg        915
Asp Glu Glu Asp Ala Phe Phe Asp Lys Ala Leu Glu Gly Phe Ala Leu
        285                 290                 295 ttt gcc ttt aac cag ggc gaa gtt tgc acc tgt ccg agt cgt gct tta        963
Phe Ala Phe Asn Gln Gly Glu Val Cys Thr Cys Pro Ser Arg Ala Leu
    300                 305                 310 gtg cag gaa tct atc tac gaa cgc ttt atg gaa cgc gcc atc cgc cgt        1011
Val Gln Glu Ser Ile Tyr Glu Arg Phe Met Glu Arg Ala Ile Arg Arg
315                 320                 325                 330 gtc gaa agc att cgt agc ggt aac ccg ctc gac agc gtg acg caa atg        1059
Val Glu Ser Ile Arg Ser Gly Asn Pro Leu Asp Ser Val Thr Gln Met
                335                 340                 345 ggc gcg cag gtt tct cac ggg caa ctg gaa acc atc ctc aac tac att        1107
Gly Ala Gln Val Ser His Gly Gln Leu Glu Thr Ile Leu Asn Tyr Ile
            350                 355                 360 gat atc ggt aaa aaa gag ggc gct gac gtg ctc aca ggc ggg cgg cgc        1155
Asp Ile Gly Lys Lys Glu Gly Ala Asp Val Leu Thr Gly Gly Arg Arg
        365                 370                 375 aag ctg ctg gaa ggt gaa ctg aaa gac ggc tac tac ctc gaa ccg acg        1203
Lys Leu Leu Glu Gly Glu Leu Lys Asp Gly Tyr Tyr Leu Glu Pro Thr
    380                 385                 390 att ctg ttt ggt cag aac aat atg cgg gtg ttc cag gag gag att ttt        1251
Ile Leu Phe Gly Gln Asn Asn Met Arg Val Phe Gln Glu Glu Ile Phe
395                 400                 405                 410 ggc ccg gtg ctg gcg gtg acc acc ttc aaa acg atg gaa gaa gcg ctg        1299
Gly Pro Val Leu Ala Val Thr Thr Phe Lys Thr Met Glu Glu Ala Leu
```

-continued

```
Gly Pro Val Leu Ala Val Thr Thr Phe Lys Thr Met Glu Glu Ala Leu
            415                 420                 425
gag ctg gcg aac gat acg caa tat ggc ctg ggc gcg ggc gtc tgg agc    1347
Glu Leu Ala Asn Asp Thr Gln Tyr Gly Leu Gly Ala Gly Val Trp Ser
            430                 435                 440 cgc aac ggt aat ctg gcc tat aag atg ggg cgc ggc ata cag gct ggg    1395
Arg Asn Gly Asn Leu Ala Tyr Lys Met Gly Arg Gly Ile Gln Ala Gly
            445                 450                 455 cgc gtg tgg acc aac tgt tat cac gct tac ccg gca cat gcg gcg ttt    1443
Arg Val Trp Thr Asn Cys Tyr His Ala Tyr Pro Ala His Ala Ala Phe
    460                 465                 470 ggt ggc tac aaa caa tca ggt atc ggt cgc gaa acc cac aag atg atg    1491
Gly Gly Tyr Lys Gln Ser Gly Ile Gly Arg Glu Thr His Lys Met Met
475                 480                 485                 490 ctg gag cat tac cag caa acc aag tgc ctg ctg gtg agc tac tcg gat    1539
Leu Glu His Tyr Gln Gln Thr Lys Cys Leu Leu Val Ser Tyr Ser Asp
                495                 500                 505 aaa ccg ttg ggg ctg ttc taagagctcg aattcgc                          1574
Lys Pro Leu Gly Leu Phe
            510
```

<210> SEQ ID NO 8
<211> LENGTH: 512
<212> TYPE: PRT
<213> ORGANISM: Escherichia coli

<400> SEQUENCE: 8

```
Met Thr Asn Pro Pro Ser Ala Gln Ile Lys Pro Gly Glu Tyr Gly
  1               5                  10                  15

Phe Pro Leu Lys Leu Lys Ala Arg Tyr Asp Asn Phe Ile Gly Gly Glu
                 20                  25                  30

Trp Val Ala Pro Ala Asp Gly Glu Tyr Tyr Gln Asn Leu Thr Pro Val
             35                  40                  45

Thr Gly Gln Leu Leu Cys Glu Val Ala Ser Ser Gly Lys Arg Asp Ile
  50                  55                  60

Asp Leu Ala Leu Asp Ala Ala His Lys Val Lys Asp Lys Trp Ala His
 65                  70                  75                  80

Thr Ser Val Gln Asp Arg Ala Ala Ile Leu Phe Lys Ile Ala Asp Arg
                 85                  90                  95

Met Glu Gln Asn Leu Glu Leu Leu Ala Thr Ala Glu Thr Trp Asp Asn
                100                 105                 110

Gly Lys Pro Ile Arg Glu Thr Ser Ala Ala Asp Val Pro Leu Ala Ile
             115                 120                 125

Asp His Phe Arg Tyr Phe Ala Ser Cys Ile Arg Ala Gln Glu Gly Gly
         130                 135                 140

Ile Ser Glu Val Asp Ser Glu Thr Val Ala Tyr His Phe His Glu Pro
145                 150                 155                 160

Leu Gly Val Val Gly Gln Ile Ile Pro Trp Asn Phe Pro Leu Leu Met
                165                 170                 175

Ala Ser Trp Lys Met Ala Pro Ala Leu Ala Ala Gly Asn Cys Val Val
             180                 185                 190

Leu Lys Pro Ala Arg Leu Thr Pro Leu Ser Val Leu Leu Leu Met Glu
         195                 200                 205

Ile Val Gly Asp Leu Leu Pro Pro Gly Val Val Asn Val Val Asn Gly
     210                 215                 220

Ala Gly Gly Val Ile Gly Glu Tyr Leu Ala Thr Ser Lys Arg Ile Ala
225                 230                 235                 240
```

Lys Val Ala Phe Thr Gly Ser Thr Glu Val Gly Gln Gln Ile Met Gln
            245                 250                 255

Tyr Ala Thr Gln Asn Ile Ile Pro Val Thr Leu Glu Leu Gly Gly Lys
            260                 265                 270

Ser Pro Asn Ile Val Phe Ala Asp Val Met Asp Glu Asp Ala Phe
            275                 280                 285

Phe Asp Lys Ala Leu Glu Gly Phe Ala Leu Phe Ala Phe Asn Gln Gly
            290                 295                 300

Glu Val Cys Thr Cys Pro Ser Arg Ala Leu Val Gln Glu Ser Ile Tyr
305                 310                 315                 320

Glu Arg Phe Met Glu Arg Ala Ile Arg Arg Val Glu Ser Ile Arg Ser
            325                 330                 335

Gly Asn Pro Leu Asp Ser Val Thr Gln Met Gly Ala Gln Val Ser His
            340                 345                 350

Gly Gln Leu Glu Thr Ile Leu Asn Tyr Ile Asp Ile Gly Lys Lys Glu
            355                 360                 365

Gly Ala Asp Val Leu Thr Gly Gly Arg Arg Lys Leu Leu Glu Gly Glu
370                 375                 380

Leu Lys Asp Gly Tyr Tyr Leu Glu Pro Thr Ile Leu Phe Gly Gln Asn
385                 390                 395                 400

Asn Met Arg Val Phe Gln Glu Glu Ile Phe Gly Pro Val Leu Ala Val
            405                 410                 415

Thr Thr Phe Lys Thr Met Glu Glu Ala Leu Glu Leu Ala Asn Asp Thr
            420                 425                 430

Gln Tyr Gly Leu Gly Ala Gly Val Trp Ser Arg Asn Gly Asn Leu Ala
            435                 440                 445

Tyr Lys Met Gly Arg Gly Ile Gln Ala Gly Arg Val Trp Thr Asn Cys
            450                 455                 460

Tyr His Ala Tyr Pro Ala His Ala Ala Phe Gly Gly Tyr Lys Gln Ser
465                 470                 475                 480

Gly Ile Gly Arg Glu Thr His Lys Met Met Leu Glu His Tyr Gln Gln
            485                 490                 495

Thr Lys Cys Leu Leu Val Ser Tyr Ser Asp Lys Pro Leu Gly Leu Phe
            500                 505                 510

<210> SEQ ID NO 9
<211> LENGTH: 5268
<212> TYPE: DNA
<213> ORGANISM: Klebsiella pneumoniae
<220> FEATURE:
<221> NAME/KEY: misc_feature
<222> LOCATION: (300)..(2153)
<223> OTHER INFORMATION: Location complement
<220> FEATURE:
<221> NAME/KEY: misc_feature
<222> LOCATION: (2166)..(2591)
<223> OTHER INFORMATION: Location complement
<220> FEATURE:
<221> NAME/KEY: misc_feature
<222> LOCATION: (2594)..(3034)
<223> OTHER INFORMATION: Location complement
<220> FEATURE:
<221> NAME/KEY: misc_feature
<222> LOCATION: (2191)..(4858)
<223> OTHER INFORMATION: Location complement

<400> SEQUENCE: 9
agcgctatat gcgttgatgc aatttctatg cgcacccgtt ctcggagcac tgtccgaccg     60
ctttggccgc cgcccagtcc tgctcgcttc gctacttgga gccactatcg actacgcgat    120

-continued

```
catggcgacc acacccgtcc tgtggatctc ccactgacca aagctggccc cggcgacccg    180
cagcgcagcg acgcagcccg cgccgaagaa aatgagcaat ccggtgccaa gaaactcggc    240
cacgcactgc ccggttaagg tagaagtctg gttcattatc ggcatcctga aatagcacgt    300
taaagagaga ggctggcgcg agcgcccgtt taattcgcct gaccggccag tagcagcccg    360
gtggcgaccg cattgcgcgg cccttctgtt ccccgaatat tgccctgccc ggcgaccacg    420
ccatagtgcg acaaggcttc cgtgataagc tgcgggatct caaagtccag cgatgagccg    480
cccaccagca ccacaaaggc gatatcgcga atggaaccgc cggtgagac ctggcgcagc     540 gcgcgcaggc agttggtgac aaacactttc tctttcgcct gccggcgcac gagacgaatt    600
ttttccagcg ggctggcgtt atcgatcggc accagttcgc cctccttgat gtacaccact    660
ttggcgaaca ccgccgggct gagggcttcc cgaaagaact ccaccgcgcc attctcgtga    720
cgaatactga acaggctttc cactttggcc agcgggtatt tttttatcgc ttccgccagc    780
gaaagatcct cgaggcccag ctcggtttta atcaacaggc tgaccatatt ccccgccccg    840
gcgagatgga ccgccgttat ctgcccctcc gcgttgacga tcgccgcatc cgtcgagccg    900
gcgccgaggt cgaggatcgc cagcggcgcc gcacagccgg gagtggttaa cgccccggcg    960
atggccatgt tggcctccac gccgcccacc accacctcgg tctgcagtcg ggcgctcagt   1020
tcgcgggcga taacctgcat ttgcagacga tccgctttca ccatcgccgc catcccgacg   1080
gcattctcca tggcgcactc gccgccatc ccgccctgca ccttgcgcgg aataaacgta    1140
tccaccgcca gcagatcctg gatgtatatc gcgctcatct catggccggt cagggacgcc   1200
attaccttgc gcaccgctc aagcatgccg ccggcgtggg tgcccggttc gccgcggatg    1260
tcgcgtaccg gagcgcaggc gctcatcgcc tgcatgatgg cttccgcgcc ctcggcgaca   1320
tcggcctctc cgcggcgctt ttcgccgcta atgtagaggt tgcccgccgg gatcacccgc   1380
gactgcacat cccctgcgg ggtcttgagc accaccgcgg aacggttgcc aatcagggcg    1440
cgggcgatgg ggacgatggc ctgggtctct ccgggctta gcccgaagaa ggtggcgatc    1500
ccgtagggat tcgacaggat ccgcaccacc tggcccggcg cggccacttc caccgccgcc   1560 attacccct cggggacctg ctccagcagc gtcacttcat ccaccaccgg cagggtttta    1620
cgcaggcggt tgttcaccag cacgccgtcg tccttttga ggatcgcgc caccacgttg     1680 atccccggt cgagcgcctc attgagccac cacacggcgt caaggaaatc gacggcgtcg    1740
tcaatcagta cgatccaccc ctcggcatac tgccgccgcg gcagcgtcgc cagccgcccg   1800
agggcgatag tcgtccccac gccaacgccc accccgcccg gcgtctgcgg gttatgaccg    1860
atcatggtcg attcggtgat aatggtctcg gtgatggtct ccatcgccac atcgccaatc    1920
accggcgcgg cttcgttaag atagatgcga gagacatcgc tcatcgacca cggtgttttc   1980 gccaggcct gctccagcgc ggcgagggtc ccggcgatat tgtcccgcgt ccctttcatg     2040
cccgtcgtcg cgacgatccc gctggcaaca aacgccctcg cctgcgggta gtcggacgcc   2100
agcgccacct cggtggtggc gttgccgata tcaatcccgg ctattaacgg catgctgacc    2160
tccgcttagc ttcctttacg cagcttatgc cgctgctgat acacttccgc cgactcccgg    2220
acaaaggcgg cattcactgt cgcatgccag gtgtgctcca gctcgtcggc gatcgccagc    2280
agctccgcct gcgaggagcg gaacgggcgc agcgcgttat agatagccag aatgcgctcg    2340
tcaggaatgg cgataagctc cgccgcgcgg cggaaattgc gcgccaccgc atggcgctgc    2400
atctgctcgg caatctgcgc ctggtactca agggtctggc gggagatccg cacatcctgc   2460
```

```
gggcccacct cgccagagag caccttctcg agggtaatat cggtcaatgg tttgccggta    2520
ggcgtcagga tatgctccgg gcagcgggtg gctaacggat aatcctgcac gcgcatggtt    2580
ttctcgctca tggtcactcc cttactaagt cgatgtgcag ggtgacgggc tcggcgtcct    2640
gcaccacatg tttggtctct ttgatatgaa atagcgcggc tttggccata aatttcggcc    2700
gcaccatctg atcgttcacc accggcaccg gcgaaggtga ctctttgcgc gcatagcgcg    2760
cagcgttttt gccaatctgc cggtaggtct ccagcgtcag cagcggcgcc tgggagaaca    2820
gctccaggtt gctgagcggc agcagatcgc gctgatggat gaccgtggtc cccttcgact    2880
ggataccgat gccgatcccc gagccgctca ggttggccgc atcccaggcc ataaaggaga    2940
cgtcggacgt gcgcagaatg cgcaccaccc gggcgtgaag cccctcttct tccaccccgg    3000
caatcagctc tttgaggatc gcgccatggg gcatatcgat cagagtgtga tgctggtgtt    3060
tatcgaaggc agggccgacg ccgatcacca cttcatcggc gcgttcatcg gcagaagcta    3120
ccccgccctc gcgggttttc agggtaaaag agggctgaat ttgggttgtc tgttgcacag    3180
gaataccgcc ttattcaatg gtgtcgggct gaaccacgcc cggaatattt ttgatctccg    3240
cccagcgttc ggcagagatg cgatagccgg tgcccggccc ctgatagtca ttgatgtcgt    3300
tgaccgcact caccacctcg aactgccgat cgagaatggc cgaggtctgc aggtaatcgc    3360
cggtgacccg ctggcgcagc atattgagaa tattgctggc gatatcctca aagccgctgc    3420
ggctcagcgc gccgacaata tcgaggccgg tgatgttgcg cttcatcatc tcttccaccg    3480
cactcagatc ctccaccacg ttacgcgcg gcatctcgtt gctgccgtgc gcgtaggtgg    3540
cggcctccac ctcctcgtcg gcgattggcg gcagcccag ctcgcggaaa accgcctgga    3600
tcgcccgcgc cgctttctgg cgaatggcaa tggtttccgc ctcggtcacc ggacgcaggc    3660
cgccgtcaac catcaggtca cgctgcagga tgttgtaatc atcaaaatct tccgcatcga    3720
agttcgagcc ggcgaacatg ttgtcgtagt tcggcaccgc gctgtagccg gagaaaataa    3780
agtcggtgcc cggcagcatc tgcatcaggg tgcgcgcggt gcggcgaata tccgagtggg    3840
agaaagtctg gtcgttggcg gacgccactt cgaggtcgag catagaggcg atcaggtttt    3900
ccgccagcac cgcccgaatg cccgacggca cagcgccggt catgccgata cagctcaccg    3960
cgccgttttg cagtccctga accccggcgc ctttagtaat gaagatgcag cgcgattcga    4020
ggtagagcat cgacttgctc tccgaatagc ccatcagcgc ttcggatccg gtgccggagg    4080
tgtagcgcat tttcaacccg cgggaggcgt aggccgaggc gaggaacgcc tttgaccacg    4140
gcgtatcatc gccgtcggta aataccgctt cggtgccgta gaccgacacc gtctcggcgt    4200
agctggttaa gccacgcatg cccagctcca gctcggtggc ctcttccacc gagcactgcg    4260
tcaacacgcc ggggcggccg cactgcgaac cgaccaacag cgccagggcg ttaaacggcg    4320
cgtagcgcgc gataccgacc gtggtctcct gttctgagaa gccgcggatc ccggcctcgg    4380
cggcgtcagc ggcaatctgc accggattat ctttgagatt ggtgacgtgg cactggttgg    4440
agggggtccg gcgggcacgc atcttctgca gcgccatcat catctccacc acgttcatct    4500
gcgccatcac ctcgaccgct ttggccgcg tgatggcggt agtgatggca atgatctcct    4560
cccggctgac gtgaatatcc accagcatac gggctatttc caccgcctcc aggcgcattg    4620
cctgctctgt gcgctcaacg ttgatcgcgt aatcggcgat aaatcggtcg atcatgtcaa    4680
actggtcccg gcgtttgccg tccagttcga cgatcagacc gttgtccact tttactgaag    4740
agaccgggtc aaaggggctg tccatggcga tcagcccctc ttcaggccac tcgccaatca    4800
gcccgtcctg attgacgggg cgctgggcca gtactgcaaa tcgtttttgat cttttcattg    4860
```

-continued

```
ttcatcggct caaaaggtga atccgcaga cggtagcgaa tacgccgggc cagcgtcgtt    4920
gccgcccggc cattaccggc aatagcggaa ctttaaatga gccagtggtg aaaaaaataa    4980
atttaatttc gtttcaattt ggcacacgaa atctaccgac agtttcacta tgaaacttta    5040
ctccggcggc aaaaataaaa aatgtgatcg cccgcaatga tataaatcaa ttaataaaaa    5100
acgcccttaa ttcgttttt ccgacgctat tttaaccta ttgactaaat catggcgggc    5160
gacaaaataa cgctgacaaa aataaagcaa gccaaccgaa tggtaatagt tttttactat    5220
cgccccctac tgactattcg cgccagcgtt atcctggtgc gggagaga              5268
```

<210> SEQ ID NO 10
<211> LENGTH: 607
<212> TYPE: PRT
<213> ORGANISM: Klebsiella pneumoniae

<400> SEQUENCE: 10

```
Met Pro Leu Ile Ala Gly Ile Asp Ile Gly Asn Ala Thr Thr Glu Val
 1               5                  10                  15

Ala Leu Ala Ser Asp Tyr Pro Gln Ala Arg Ala Phe Val Ala Ser Gly
             20                  25                  30

Ile Val Ala Thr Thr Gly Met Lys Gly Thr Arg Asp Asn Ile Ala Gly
         35                  40                  45

Thr Leu Ala Ala Leu Glu Gln Ala Leu Ala Lys Thr Pro Trp Ser Met
     50                  55                  60

Ser Asp Val Ser Arg Ile Tyr Leu Asn Glu Ala Ala Pro Val Ile Gly
 65                  70                  75                  80

Asp Val Ala Met Glu Thr Ile Thr Glu Thr Ile Thr Glu Ser Thr
                 85                  90                  95

Met Ile Gly His Asn Pro Gln Thr Pro Gly Gly Val Gly Val Gly Val
                100                 105                 110

Gly Thr Thr Ile Ala Leu Gly Arg Leu Ala Thr Leu Pro Ala Ala Gln
            115                 120                 125

Tyr Ala Glu Gly Trp Ile Val Leu Ile Asp Asp Ala Val Asp Phe Leu
        130                 135                 140

Asp Ala Val Trp Trp Leu Asn Glu Ala Leu Asp Arg Gly Ile Asn Val
145                 150                 155                 160

Val Ala Ala Ile Leu Lys Lys Asp Asp Gly Val Leu Val Asn Asn Arg
                165                 170                 175

Leu Arg Lys Thr Leu Pro Val Val Asp Glu Val Thr Leu Leu Glu Gln
            180                 185                 190

Val Pro Glu Gly Val Met Ala Ala Val Glu Val Ala Ala Pro Gly Gln
        195                 200                 205

Val Val Arg Ile Leu Ser Asn Pro Tyr Gly Ile Ala Thr Phe Phe Gly
    210                 215                 220

Leu Ser Pro Glu Glu Thr Gln Ala Ile Val Pro Ile Ala Arg Ala Leu
225                 230                 235                 240

Ile Gly Asn Arg Ser Ala Val Val Leu Lys Thr Pro Gln Gly Asp Val
                245                 250                 255

Gln Ser Arg Val Ile Pro Ala Gly Asn Leu Tyr Ile Ser Gly Glu Lys
            260                 265                 270

Arg Arg Gly Glu Ala Asp Val Ala Glu Gly Ala Glu Ala Ile Met Gln
        275                 280                 285

Ala Met Ser Ala Cys Ala Pro Val Arg Asp Ile Arg Gly Glu Pro Gly
    290                 295                 300
```

-continued

Thr His Ala Gly Gly Met Leu Glu Arg Val Arg Lys Val Met Ala Ser
305                 310                 315                 320

Leu Thr Gly His Glu Met Ser Ala Ile Tyr Ile Gln Asp Leu Leu Ala
            325                 330                 335

Val Asp Thr Phe Ile Pro Arg Lys Val Gln Gly Met Ala Gly Glu
            340                 345                 350

Cys Ala Met Glu Asn Ala Val Gly Met Ala Ala Met Val Lys Ala Asp
            355                 360                 365

Arg Leu Gln Met Gln Val Ile Ala Arg Glu Leu Ser Ala Arg Leu Gln
    370                 375                 380

Thr Glu Val Val Gly Gly Val Glu Ala Asn Met Ala Ile Ala Gly
385                 390                 395                 400

Ala Leu Thr Thr Pro Gly Cys Ala Ala Pro Leu Ala Ile Leu Asp Leu
            405                 410                 415

Gly Ala Gly Ser Thr Asp Ala Ala Ile Val Asn Ala Glu Gly Gln Ile
            420                 425                 430

Thr Ala Val His Leu Ala Gly Ala Gly Asn Met Val Ser Leu Leu Ile
            435                 440                 445

Lys Thr Glu Leu Gly Leu Glu Asp Leu Ser Leu Ala Glu Ala Ile Lys
    450                 455                 460

Lys Tyr Pro Leu Ala Lys Val Glu Ser Leu Phe Ser Ile Arg His Glu
465                 470                 475                 480

Asn Gly Ala Val Glu Phe Phe Arg Glu Ala Leu Ser Pro Ala Val Phe
            485                 490                 495

Ala Lys Val Val Tyr Ile Lys Glu Gly Glu Leu Val Pro Ile Asp Asn
            500                 505                 510

Ala Ser Pro Leu Glu Lys Ile Arg Leu Val Arg Arg Gln Ala Lys Glu
            515                 520                 525

Lys Val Phe Val Thr Asn Cys Leu Arg Ala Leu Arg Gln Val Ser Pro
    530                 535                 540

Gly Gly Ser Ile Arg Asp Ile Ala Phe Val Val Leu Val Gly Gly Ser
545                 550                 555                 560

Ser Leu Asp Phe Glu Ile Pro Gln Leu Ile Thr Glu Ala Leu Ser His
            565                 570                 575

Tyr Gly Val Val Ala Gly Gln Gly Asn Ile Arg Gly Thr Glu Gly Pro
            580                 585                 590

Arg Asn Ala Val Ala Thr Gly Leu Leu Leu Ala Gly Gln Ala Asn
    595                 600                 605

<210> SEQ ID NO 11
<211> LENGTH: 141
<212> TYPE: PRT
<213> ORGANISM: Klebsiella pneumoniae

<400> SEQUENCE: 11

Met Ser Glu Lys Thr Met Arg Val Gln Asp Tyr Pro Leu Ala Thr Arg
1               5                   10                  15

Cys Pro Glu His Ile Leu Thr Pro Thr Gly Lys Pro Leu Thr Asp Ile
            20                  25                  30

Thr Leu Glu Lys Val Leu Ser Gly Glu Val Gly Pro Gln Asp Val Arg
        35                  40                  45

Ile Ser Arg Gln Thr Leu Glu Tyr Gln Ala Gln Ile Ala Glu Gln Met
    50                  55                  60

Gln Arg His Ala Val Ala Arg Asn Phe Arg Arg Ala Ala Glu Leu Ile

```
                65                  70                  75                  80
Ala Ile Pro Asp Glu Arg Ile Leu Ala Ile Tyr Asn Ala Leu Arg Pro
                    85                  90                  95

Phe Arg Ser Ser Gln Ala Glu Leu Leu Ala Ile Ala Asp Glu Leu Glu
                100                 105                 110

His Thr Trp His Ala Thr Val Asn Ala Ala Phe Val Arg Glu Ser Ala
            115                 120                 125

Glu Val Tyr Gln Gln Arg His Lys Leu Arg Lys Gly Ser
    130                 135                 140

<210> SEQ ID NO 12
<211> LENGTH: 146
<212> TYPE: PRT
<213> ORGANISM: Klebsiella pneumoniae

<400> SEQUENCE: 12

Met Pro His Gly Ala Ile Leu Lys Glu Leu Ile Ala Gly Val Glu Glu
1               5                   10                  15

Glu Gly Leu His Ala Arg Val Val Arg Ile Leu Arg Thr Ser Asp Val
                20                  25                  30

Ser Phe Met Ala Trp Asp Ala Ala Asn Leu Ser Gly Ser Gly Ile Gly
            35                  40                  45

Ile Gly Ile Gln Ser Lys Gly Thr Thr Val Ile His Gln Arg Asp Leu
        50                  55                  60

Leu Pro Leu Ser Asn Leu Glu Leu Phe Ser Gln Ala Pro Leu Leu Thr
65                  70                  75                  80

Leu Glu Thr Tyr Arg Gln Ile Gly Lys Asn Ala Ala Arg Tyr Ala Arg
                85                  90                  95

Lys Glu Ser Pro Ser Pro Val Pro Val Asn Asp Gln Met Val Arg
                100                 105                 110

Pro Lys Phe Met Ala Lys Ala Ala Leu Phe His Ile Lys Glu Thr Lys
            115                 120                 125

His Val Val Gln Asp Ala Glu Pro Val Thr Leu His Ile Asp Leu Val
        130                 135                 140

Arg Glu
145

<210> SEQ ID NO 13
<211> LENGTH: 555
<212> TYPE: PRT
<213> ORGANISM: Klebsiella pneumoniae

<400> SEQUENCE: 13

Met Lys Arg Ser Lys Arg Phe Ala Val Leu Ala Gln Arg Pro Val Asn
1               5                   10                  15

Gln Asp Gly Leu Ile Gly Glu Trp Pro Glu Glu Gly Leu Ile Ala Met
                20                  25                  30

Asp Ser Pro Phe Asp Pro Val Ser Ser Val Lys Val Asp Asn Gly Leu
            35                  40                  45

Ile Val Glu Leu Asp Gly Lys Arg Arg Asp Gln Phe Asp Met Ile Asp
        50                  55                  60

Arg Phe Ile Ala Asp Tyr Ala Ile Asn Val Glu Arg Thr Glu Gln Ala
65                  70                  75                  80

Met Arg Leu Glu Ala Val Glu Ile Ala Arg Met Leu Val Asp Ile His
                85                  90                  95

Val Ser Arg Glu Glu Ile Ile Ala Ile Thr Thr Ala Ile Thr Pro Ala
```

-continued

```
            100                 105                 110
Lys Ala Val Glu Val Met Ala Gln Met Asn Val Glu Met Met Met
        115                 120                 125
Ala Leu Gln Lys Met Arg Ala Arg Arg Thr Pro Ser Asn Gln Cys His
        130                 135             140
Val Thr Asn Leu Lys Asp Asn Pro Val Gln Ile Ala Asp Ala Ala
145                 150                 155                 160
Glu Ala Gly Ile Arg Gly Phe Ser Glu Gln Glu Thr Thr Val Gly Ile
                165                 170                 175
Ala Arg Tyr Ala Pro Phe Asn Ala Leu Ala Leu Leu Val Gly Ser Gln
            180                 185                 190
Cys Gly Arg Pro Gly Val Leu Thr Gln Cys Ser Val Glu Glu Ala Thr
        195                 200                 205
Glu Leu Glu Leu Gly Met Arg Gly Leu Thr Ser Tyr Ala Glu Thr Val
        210                 215                 220
Ser Val Tyr Gly Thr Glu Ala Val Phe Thr Asp Gly Asp Asp Thr Pro
225                 230                 235                 240
Trp Ser Lys Ala Phe Leu Ala Ser Ala Tyr Ala Ser Arg Gly Leu Lys
                245                 250                 255
Met Arg Tyr Thr Ser Gly Thr Gly Ser Glu Ala Leu Met Gly Tyr Ser
            260                 265                 270
Glu Ser Lys Ser Met Leu Tyr Leu Glu Ser Arg Cys Ile Phe Ile Thr
        275                 280                 285
Lys Gly Ala Gly Val Gln Gly Leu Gln Asn Gly Ala Val Ser Cys Ile
        290                 295                 300
Gly Met Thr Gly Ala Val Pro Ser Gly Ile Arg Ala Val Leu Ala Glu
305                 310                 315                 320
Asn Leu Ile Ala Ser Met Leu Asp Leu Glu Val Ala Ser Ala Asn Asp
                325                 330                 335
Gln Thr Phe Ser His Ser Asp Ile Arg Arg Thr Ala Arg Thr Leu Met
            340                 345                 350
Gln Met Leu Pro Gly Thr Asp Phe Ile Phe Ser Gly Tyr Ser Ala Val
        355                 360                 365
Pro Asn Tyr Asp Asn Met Phe Ala Gly Ser Asn Phe Asp Ala Glu Asp
370                 375                 380
Phe Asp Asp Tyr Asn Ile Leu Gln Arg Asp Leu Met Val Asp Gly Gly
385                 390                 395                 400
Leu Arg Pro Val Thr Glu Ala Glu Thr Ile Ala Ile Arg Gln Lys Ala
                405                 410                 415
Ala Arg Ala Ile Gln Ala Val Phe Arg Glu Leu Gly Leu Pro Pro Ile
            420                 425                 430
Ala Asp Glu Glu Val Glu Ala Thr Tyr Ala His Gly Ser Asn Glu
        435                 440                 445
Met Pro Pro Arg Asn Val Val Glu Asp Leu Ser Ala Val Glu Glu Met
        450                 455                 460
Met Lys Arg Asn Ile Thr Gly Leu Asp Ile Val Gly Ala Leu Ser Arg
465                 470                 475                 480
Ser Gly Phe Glu Asp Ile Ala Ser Asn Ile Leu Asn Met Leu Arg Gln
                485                 490                 495
Arg Val Thr Gly Asp Tyr Leu Gln Thr Ser Ala Ile Leu Asp Arg Gln
            500                 505                 510
Phe Glu Val Val Ser Ala Val Asn Asp Ile Asn Asp Tyr Gln Gly Pro
        515                 520                 525
```

Gly Thr Gly Tyr Arg Ile Ser Ala Glu Arg Trp Ala Glu Ile Lys Asn
            530                 535                 540

Ile Pro Gly Val Val Gln Pro Asp Thr Ile Glu
545                 550                 555

<210> SEQ ID NO 14
<211> LENGTH: 56
<212> TYPE: DNA
<213> ORGANISM: Escherichia coli

<400> SEQUENCE: 14
gctaccatgg cttaaccggt accaaggaga tatcatatgt cagtacccgt tcaaca        56

<210> SEQ ID NO 15
<211> LENGTH: 59
<212> TYPE: DNA
<213> ORGANISM: Escherichia coli

<400> SEQUENCE: 15
gcctcgagtc tagagccgtc gacgggaatt cgagctctta agactgtaaa taaaccacc    59

<210> SEQ ID NO 16
<211> LENGTH: 46
<212> TYPE: DNA
<213> ORGANISM: Saccharomyces cerevasiae

<400> SEQUENCE: 16
gcggtaccaa ggaggtatca tatgttcagt agatctacgc tctgct                  46

<210> SEQ ID NO 17
<211> LENGTH: 34
<212> TYPE: DNA
<213> ORGANISM: Saccharomyces cerevasiae

<400> SEQUENCE: 17
gcgaattcga gctcttactc gtccaatttg gcac                               34

<210> SEQ ID NO 18
<211> LENGTH: 35
<212> TYPE: DNA
<213> ORGANISM: Homo sapiens

<400> SEQUENCE: 18
gcggtaccaa ggaggtatca tatgtcagcc gccgc                              35

<210> SEQ ID NO 19
<211> LENGTH: 39
<212> TYPE: DNA
<213> ORGANISM: Homo sapiens

<400> SEQUENCE: 19
gcgaattcga gctcttatga gttcttctga ggcactttg                          39

<210> SEQ ID NO 20
<211> LENGTH: 44
<212> TYPE: DNA
<213> ORGANISM: Escherichia coli

<400> SEQUENCE: 20
gcggtaccaa ggaggtatca tatgaccaat aatccccctt cagc                    44

<210> SEQ ID NO 21

-continued

```
<211> LENGTH: 38
<212> TYPE: DNA
<213> ORGANISM: Escherichia coli

<400> SEQUENCE: 21
gcgaattcga gctcttagaa cagccccaac ggtttatc                              38

<210> SEQ ID NO 22
<211> LENGTH: 20
<212> TYPE: DNA
<213> ORGANISM: Escherichia coli

<400> SEQUENCE: 22
atcccgccgt taaccaccat                                                  20

<210> SEQ ID NO 23
<211> LENGTH: 34
<212> TYPE: DNA
<213> ORGANISM: Escherichia coli

<400> SEQUENCE: 23
gcggtaccat tgttatccgc tcacaattcc acac                                  34
```